US010271832B2

United States Patent
O'Neil et al.

(10) Patent No.: US 10,271,832 B2
(45) Date of Patent: Apr. 30, 2019

(54) METHODS AND DEVICES FOR SPINAL CORRECTION

(71) Applicant: DEPUY SYNTHES PRODUCTS, INC., Raynham, MA (US)

(72) Inventors: Michael J. O'Neil, West Barnstable, MA (US); Roman Lomeli, Plymouth, MA (US); John Riley Hawkins, Cumberland, RI (US); Christopher Ramsay, West Wareham, MA (US); Zoher Bootwala, Foxboro, MA (US); Jennifer DiPietro, North Easton, MA (US); John Griffin, Boston, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 74 days.

(21) Appl. No.: 15/259,157

(22) Filed: Sep. 8, 2016

(65) Prior Publication Data

US 2016/0374660 A1 Dec. 29, 2016

Related U.S. Application Data

(62) Division of application No. 14/247,876, filed on Apr. 8, 2014, now Pat. No. 9,456,817.

(51) Int. Cl.
*A61B 5/00* (2006.01)
*A61F 2/44* (2006.01)
(Continued)

(52) U.S. Cl.
CPC ........ *A61B 17/025* (2013.01); *A61B 1/00087* (2013.01); *A61B 1/3135* (2013.01);
(Continued)

(58) Field of Classification Search
CPC ........ A61F 2/46; A61F 2/4611; A61F 2/4684; A61B 2017/0256; A61B 2090/065
See application file for complete search history.

(56) References Cited

U.S. PATENT DOCUMENTS 6,425,920 B1 * 7/2002 Hamada ............. A61B 17/1604
623/17.16
7,267,687 B2 9/2007 McGurkin, Jr.
(Continued)

FOREIGN PATENT DOCUMENTS

CN 102014799 A 4/2011
CN 103533904 A 1/2014
(Continued)

OTHER PUBLICATIONS

Written Opinion of the International Searching Authority, Application No. PCT/US2015/024972; date received Sep. 2, 2015, 5 pages.
(Continued)

*Primary Examiner* — Ellen C Hammond
(74) *Attorney, Agent, or Firm* — Raymond N. Scott, Jr.

(57) ABSTRACT

An expandable trial can include an inferior portion, a superior portion, and a middle expanding portion as well as load cells for monitoring the load on the trial. The trial may also include recesses on its lateral sides to provide spacing to accommodate a disc removal tool so tissue can be cleared monitoring load. In addition, neural foramen spacing can be monitoring to provide information about how much neural release has been achieved as the disc is cleaned and the spine is positioned and repositioned.

14 Claims, 19 Drawing Sheets

(51) Int. Cl.
  *A61F 2/46*  (2006.01)
  *A61B 17/02*  (2006.01)
  *A61B 90/00*  (2016.01)
  *A61B 1/00*  (2006.01)
  *A61B 1/313*  (2006.01)
  *A61B 8/08*  (2006.01)
  *A61B 8/12*  (2006.01)
  *A61B 5/107*  (2006.01)
  *A61B 17/00*  (2006.01)
  *A61B 17/16*  (2006.01)
  *A61F 2/30*  (2006.01)
  *A61B 5/055*  (2006.01)
  *A61B 34/20*  (2016.01)

(52) U.S. Cl.
  CPC .......... *A61B 5/1076* (2013.01); *A61B 5/4566* (2013.01); *A61B 8/0858* (2013.01); *A61B 8/0875* (2013.01); *A61B 8/12* (2013.01); *A61B 90/06* (2016.02); *A61F 2/44* (2013.01); *A61F 2/442* (2013.01); *A61F 2/4657* (2013.01); *A61F 2/4684* (2013.01); *A61B 5/0071* (2013.01); *A61B 5/055* (2013.01); *A61B 5/6853* (2013.01); *A61B 17/1671* (2013.01); *A61B 2017/00022* (2013.01); *A61B 2017/00106* (2013.01); *A61B 2017/0256* (2013.01); *A61B 2034/2055* (2016.02); *A61B 2090/065* (2016.02); *A61B 2505/05* (2013.01); *A61B 2562/04* (2013.01); *A61F 2/4611* (2013.01); *A61F 2002/30405* (2013.01); *A61F 2002/30471* (2013.01); *A61F 2002/30507* (2013.01); *A61F 2002/30515* (2013.01); *A61F 2002/30556* (2013.01); *A61F 2002/4633* (2013.01); *A61F 2002/4658* (2013.01); *A61F 2002/4666* (2013.01)

(56) References Cited

U.S. PATENT DOCUMENTS

| | | | |
|---|---|---|---|
| 7,507,255 B2 * | 3/2009 | Ralph | A61B 17/025 623/17.11 |
| 8,986,386 B2 | 3/2015 | Oglaza et al. | |
| 8,986,387 B1 * | 3/2015 | To | A61F 2/4611 623/17.15 |
| 9,271,842 B2 * | 3/2016 | Davenport | A61F 2/44 |
| 2005/0038511 A1 | 2/2005 | Martz et al. | |
| 2007/0055378 A1 | 3/2007 | Ankney et al. | |
| 2008/0234740 A1 | 9/2008 | Landry et al. | |
| 2008/0269756 A1 | 10/2008 | Tomko et al. | |
| 2009/0105828 A1 | 4/2009 | Gimbel et al. | |
| 2009/0216331 A1 * | 8/2009 | Grotz | A61F 2/442 623/17.16 |
| 2009/0234456 A1 | 9/2009 | Nycz | |
| 2010/0057204 A1 * | 3/2010 | Kadaba | A61F 2/442 623/17.12 |
| 2010/0292801 A1 | 11/2010 | Hansell et al. | |
| 2015/0182288 A1 * | 7/2015 | Greenwald | A61F 2/442 606/279 |

FOREIGN PATENT DOCUMENTS

| | | |
|---|---|---|
| JP | 2005504584 | 2/2005 |
| JP | 2010516344 | 5/2010 |
| JP | 2011512893 | 4/2011 |
| JP | 2012520108 | 9/2012 |
| WO | 2012122294 | 9/2012 |
| WO | WO 2013/158960 A1 | 10/2013 |

OTHER PUBLICATIONS

Notification of Transmittal of the International Search Report and Written Opinion Application No. PCT/US2015/024972; dated Aug. 26, 2015, 7 pages.
U.S. Appl. No. 61/702,073, filed Sep. 17, 2012 and entitled "Systems and Methods for Surgical Planning, Support, and Review".
U.S. Appl. No. 61/739,514, filed Dec. 19, 2012 and entitled "Systems and Methods for Surgical Planning, Support, and Review".
U.S. Appl. No. 13/803,763, filed Mar. 14, 2013 and entitled "Systems and Methods for Surgical and Interventional Planning, Support, Postoperative Follow-Up, and Functional Recovery Tracking."
JP Office Action dated Oct. 30, 2018 with English translation.

\* cited by examiner

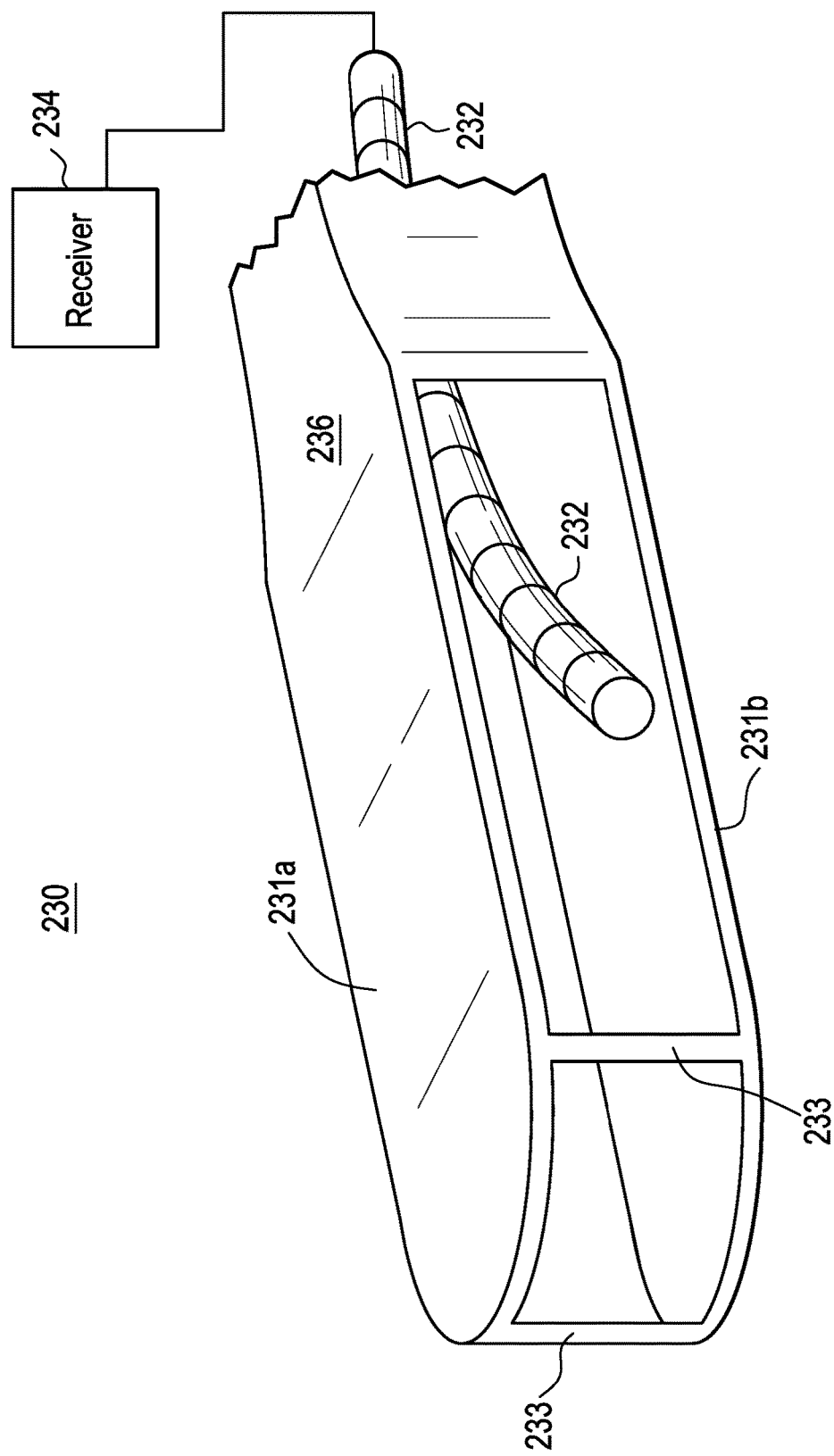

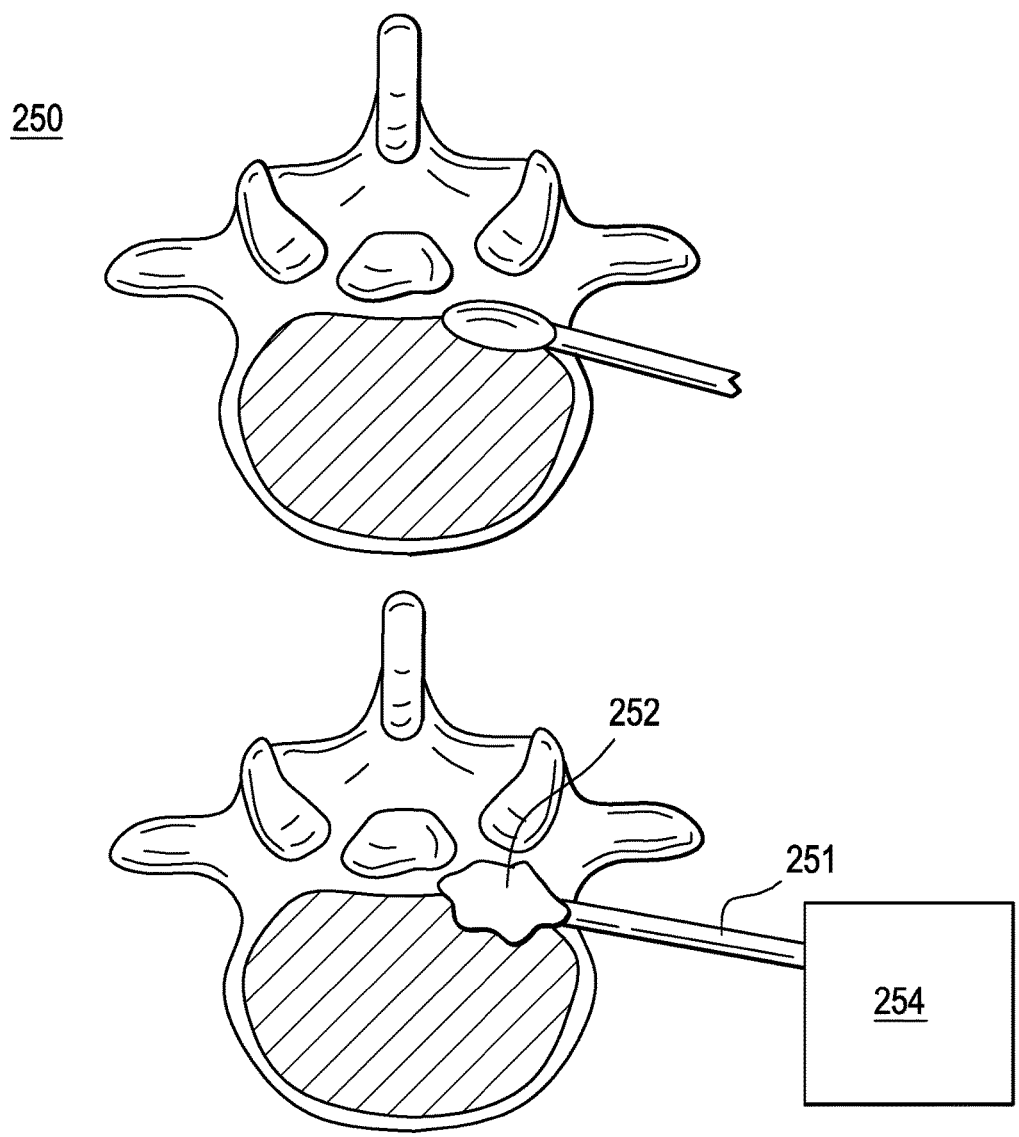

METHODS AND DEVICES FOR SPINAL CORRECTION

This application is a divisional of U.S. patent application Ser. No. 14/247,876 filed Apr. 8, 2014, the disclosures of all of which are hereby incorporated by reference as if set forth in their entirety herein.

TECHNICAL FIELD

The present disclosure relates to spinal correction methods and systems including expandable trial implants and techniques for monitoring the amount of neural spacing achieved and optionally monitoring the amount of disc space distraction and the force on the vertebral endplates.

BACKGROUND

The human spine is a series of bony vertebral bodies separated by flexible discs called "intervertebral discs." The discs contain a compressible, flexible jelly-like center called the nucleus pulposus. This flexibility allows the spine to bend and twist. The annulus fibrosus is a tougher, fibrous material that surrounds and contains the nucleus, which otherwise could be extruded into other parts of the body.

The human skeleton provides an architectural structure for the human body. The human spine provides not only a mechanical structure for supporting a person's weight, but also provides passages for the "wires" of the nervous system. The spine provides spacing for the nerves to travel from the brain to other parts of the body. The majority of this spacing is the spinal canal which contains and protects the spinal cord. The spine also defines, at each level of the spine, spacing for nerves roots to branch off from the spinal cord and travel to other parts of the body. Intervertebral discs between the vertebral bodies are critical in providing the appropriate amount of spacing between the vertebral bodies to allow room for these nerve roots. If the discs begin to collapse from their normal height, nerve roots may become compressed and cause pain.

The discs also help provide alignment of the vertebral bodies, keeping the spinal canal as a relatively smooth passage for the spinal cord. If the discs become misaligned, the spinal canal may become disjointed and extremely narrowed in portions. If it becomes too narrowed, the spinal cord may become compressed and cause pain. Spondylolysis is an example of one condition which can affect the spacing in the spinal canal. In spondylolysis, one vertebral body slips forward relative to another vertebral body. This can result in a narrowing of the spinal canal and compression of the spinal cord.

Other spinal disorders can also result in nerve compression. For example, degenerative disc disease (DDD) can result in a herniated disc. A herniated disc occurs when a portion of the nucleus is extruded from the disc space. This extrusion might impinge on a nerve and cause pain. Also, the extrusion of too much of the nucleus may result in a reduction in the height of the disc, and cause narrowing of the spacing available for nerve roots.

A common method of managing these problems is to remove the problematic disc and replace it with a device that restores the disc height and allows for bone growth therethrough. This results in the fusion of two or more adjacent vertebrae. The devices used in this procedure are commonly referred to as "fusion devices" or "fusion cages".

In a fusion procedure, a surgeon first accesses the intervertebral disc space. Next, the surgeon clears out a portion of the intervertebral disc space to make room for the fusion device (or cage). The surgeon may determine the appropriate size fusion cage by using trial implants and "testing" its fit via tactile and visual assessment, often assisted by fluoroscopy. Neuromonitoring can also be used to confirm that there is no significant injury or damage to the neural structures. For example, neuromonitoring can be used to test the response and latency of the nerves which can give an indication of how healthy the nerve is. However, neuromonitoring does not determine if the procedure has created enough "space" (referred to as neural release) to relieve the compression on the nerve.

SUMMARY

An expandable trial can include an inferior portion, a superior portion, and a middle expanding portion as well as load cells for monitoring the load on the trial. The trial may also include recesses on its lateral sides to provide spacing to accommodate a disc removal tool so tissue can be cleared while monitoring load. In addition, neural foramen spacing can be monitored to provide information about how much neural release has been achieved as the disc is cleaned and the spine is positioned and repositioned.

DESCRIPTION OF THE FIGURES

FIG. 1b is a system diagram of an exemplary embodiment of a system for spinal correction which may be used in connection with the method of FIG. 1a.

FIG. 2a shows an exemplary embodiment of an image-guided surgery system which may be used in connection with the method of FIG. 1a.

FIG. 2b shows an exemplary embodiment of a mylogram tracking system which may be used in connection with the method of FIG. 1a.

FIG. 2c shows an exemplary embodiment of a direct visualization system which may be used in connection with the method of FIG. 1a.

FIG. 2d shows an exemplary embodiment of an ultrasonic detection system which may be used in connection with the method of FIG. 1a.

FIG. 2e shows an exemplary embodiment of a direct visualization system which may be used in connection with the method of FIG. 1a.

FIG. 2f shows an exemplary embodiment of a dye-based mylogram tracking system which may be used in connection with the method of FIG. 1a.

FIGS. 3a and 3b show an exemplary embodiment of an expandable trial implant which may be used in connection with the method of FIG. 1a.

FIGS. 4a, 4b, and 4c show exemplary embodiments of a visual display system providing a top view of load information from an expandable trial implant which may be used in connection with the method of FIG. 1a.

FIGS. 5a through 5h show an exemplary embodiment of another exemplary embodiment of an expandable trial implant which may be used in connection with the method of FIG. 1a FIGS. 6a through 6h show another exemplary embodiment of an expandable trial implant which may be used in connection with the method of FIG. 1a.

DETAILED DESCRIPTION OF THE FIGURES

Figure 1A:
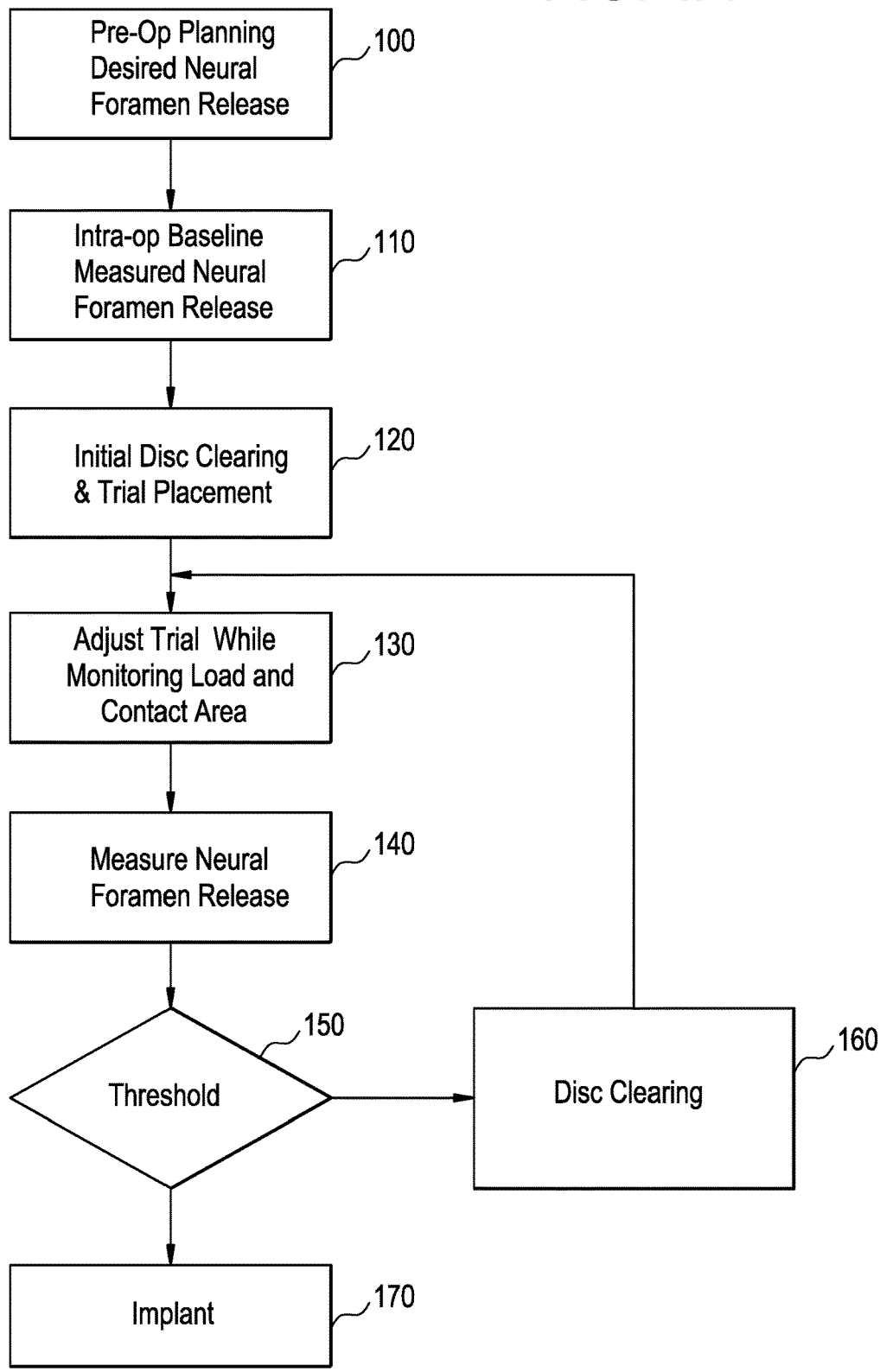
FIG. 1a is a flow chart of an exemplary embodiment of a method for spinal correction using an expandable trial implant and monitoring the amount of neural spacing achieved.

FIG. 1a is a flow chart of an exemplary embodiment of a method for spinal correction 10 using an expandable trial implant and including monitoring an amount of neural spacing achieved. While various method steps are shown, it is not mandatory for each step to be performed, for example, in some cases an intra-operative baseline may not be determined. Other steps may also be omitted.

Figure 1B:
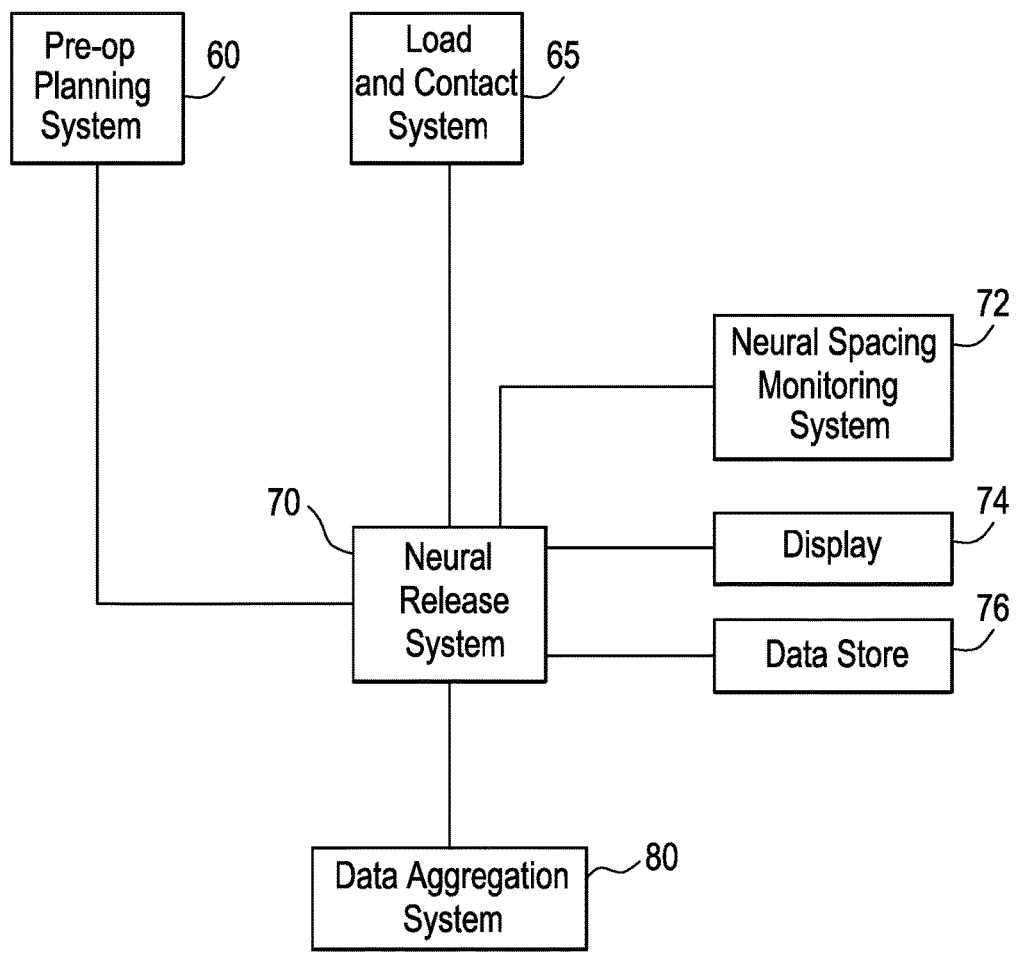

Spinal correction method 10 may be implemented with a spinal correction system 50 shown in FIG. 1b. As shown in FIG. 1b, spinal correction system 50 includes a neural release system 70. Neural release system 70 includes a neural spacing monitoring system 72 which determines information representative of an amount of neural spacing achieved. Neural spacing monitoring system 72 may be implemented in various embodiments, such as will be discussed in connection with FIGS. 2a through 2f. Neural release system 70 also includes display device 74 and data store 76. Neural release system 70 can also communicate with data aggregation system 80 which aggregates and evaluates medical data. Data aggregation system 80 may be the system described in any of the following patent applications, each of which are herein incorporated by reference in their entirety: U.S. Patent Application Ser. No. 61/702,073, filed Sep. 17, 2012 and entitled "Systems and Methods for Surgical Planning, Support, and Review"; U.S. Patent Application Ser. No. 61/739,514, filed Dec. 19, 2012 and entitled "Systems and Methods for Surgical Planning, Support, and Review"; and U.S. patent application Ser. No. 13/803,763, filed Mar. 14, 2013 and entitled "Systems and Methods for Surgical and Interventional Planning, Support, Postoperative Follow-Up, and Functional Recovery Tracking." Data aggregation system 80 may store data from the neural spacing monitoring system 72 and neural release system 70, along with other post-operative data, and use a combination of data to predict the likelihood of success for fusion and/or pain relief of a future surgery for a particular patient. The prediction of likelihood of success may be based on past outcomes of surgeries on other patients and on information about the particular patient. Data aggregation system 80 may use any of the techniques and algorithms described therein for making such predictions.

Spinal correction system 50 includes a pre-operative planning system 60 which may be implemented in various embodiments discussed further below. Spinal correction system 50 also includes load and contact system 65 which determines the load on the expandable trial implant at various portions of the implant and also determines the portions of the trial implant that have contacted the endplates of the vertebral body. While various components are shown, it is not mandatory for spinal correction system 50 to include each component/system. Moreover, while the spinal correction system 50 is shown as including separate physical components, the system 50 could be implemented in one physical component or could be distributed among various components in manners other than as illustrated.

Turning back to method 10 of FIG. 1a, as shown at step 100, pre-operative planning is performed using pre-operative planning system 60. Pre-operative planning system 60 may include an imaging system (e.g., magnetic-resonance imaging (MRI) systems, x-ray systems, fluoroscopy systems, computed tomography (CT) systems, etc.) to estimate an amount of existing (pre-operative) neural spacing and existing neural compression as well as the amount of disc space achieved by the expandable implant. This information may be communicated to neural release system 70 for determination of a planned amount spinal correction and a planned amount of neural release. The planned amount of spinal correction and the planned amount of neural release may be based on the aggregation of data in data aggregation system 80 which includes historical data on spinal surgeries and their outcomes for pain relief.

The existing amount of spinal abnormality and planned amount of spinal correction may be described using various parameters. Pre-operative planning system 60 may calculate an existing pre-operative disc space height (which may include disc space height at various portions of the disc, e.g., posterior, anterior, lateral, central, etc.). Pre-operative planning system 60 may also calculate an existing pre-operative disc space angle (which may include the angle of the superior endplate along various planes, the angle of the inferior endplate along various planes, the angles between both, etc.). This angle may represent the existing pre-operative amount of lordosis, kyphosis, sagittal balance, and coronal balance. The existing pre-operative parameters may be calculated based on images from a CT, MRI, or other non-invasive techniques.

Neural release system 70 (or alternatively pre-operative planning system 60 or data aggregation system 80) may calculate a planned post-operative disc space height, or change in height, and angle, or change in angle (as well as other parameters such as a desired or planned sagittal and/or anterior-posterior adjustment of one vertebral body relative to another to correct for a spondylolysis). The planned pre-operative parameters may be calculated based on images from a CT, MRI, etc. as well as based on empirical data of previous spine surgeries. The empirical data may include both pre- and post-operative disc space height and angle (and other parameters) as well as data representative of the outcomes of prior surgeries. The outcomes may include post-operative pain data, fusion data, etc. The calculation may be performed by pre-operative planning system 60 with or without information from data aggregation system 80.

In addition to calculating planned or desired post-operative geometries, neural release system 70 (or alternatively pre-operative planning system 60 or data aggregation system 80) may calculate a desired or planned post-operative amount of neural release. The planned amount of neural release may take a variety of forms depending on the type of neural release monitoring system to be used intra-operatively. The planned post-operative amount of neural release may be calculated based on images from a CT, MRI, etc. and may be based on empirical data of previous spine surgeries, e.g., using information from data aggregation system 80. The empirical data may include both pre- and post-operative disc space height and angle and alignment as well as data representative of the outcomes of prior surgeries. The outcomes may include post-operative pain indications, fusion indications, etc.

As shown at step 110, intra-operative baseline measurements are taken and received by neural release system 70. For example, after the patient is positioned, the surgeon may obtain a baseline of actual neural spacing (e.g., actual neural foramen size, or information representative of neural foramen size such as pressure, size calculations based on direct visualization, etc.). This may be accomplished using neural spacing monitoring system 72. This information, because it is determined intra-operatively might be more accurate than the information obtained in step 100 which was determined pre-operatively. Neural spacing monitoring system 72 may also determine actual neural compression (e.g., size reduction of the nerve, fluid pressure differential across the neural compression, or other information representative of actual neural compression). Neural release system 70 uses the intra-operative baseline measurements to determine an updated planned amount of neural release.

Neural release system 70 may calculate foramen spacing using a variety of algorithms based on intra-operative information provided by neural spacing monitoring system 72 and possibly based on historical and/or empirical information stored, for example, in data aggregation system 80. Neural release system 70 may calculate foramen spacing using foramen height measurements and foramen width measurements. Neural release system 70 may calculate a foramen area based on the measured height and width. Neural release system 70 may also calculate a foramen area based on multiple measured heights and widths which may be averaged and may provide a more accurate determination of foramen area. Neural release system 70 may further calculate a foramen volume based on the measured height and width along with a measure depth. Neural release system 70 may also calculate a foramen area based on multiple measured heights and widths and depths which may be averaged and may provide a more accurate determination of foramen volume. As another alternative, only foramen height may be used as representative of neural release.

Neural release system 70 may calculate a foramen area and/or volume based on geometric information received from imaging systems, e.g., such as with ultrasonic detection system 240 (described in more detail below), or the measurements may be inferred based on measurements that don't provide geometric information regarding the foramen area and/or volume. For example, neural release system 70 may receive pressure information from pressure system 220 (described in more detail below). Neural release system 70 may calculate or estimate a foramen area or volume based on historical and/or empirical data that relates pressure to foramen area or volume. This information may be stored, for example, in data aggregation system 80. Rather than converting from pressure information to area and/or volume information, neural release system 70 may use only pressure information which can be representative of foramen geometric information. As discussed in more detail below, for example, neural release system 70 may compare the measured pressure from pressure system 220 to a pressure threshold rather than converting to foramen area and comparing it to an area threshold.

Neural release system 70 may also include both pre-operative and intra-operative information in the calculation of foramen area and/or foramen volume or other information representative of foramen area and/or foramen volume (e.g., pressure). For example, neural release system 70 may adjust pre-operative measurements based on intra-operative information. The adjustment may be ratio adjustments or additive or subtractive adjustments to the pre-operative information and may include limits on the magnitude of the overall adjustment, e.g., to protect against erroneous intra-operative measurements.

Neural release system 70 may also receive measurements of disc height and use those measurements in determining if the planned or desired neural release has been achieved. Neural release system 70 may include disc height in an overall calculation that represent neural foramen spacing or may treat disc height as a separate parameter with its own separate threshold. Neural release system 70 may use foramen height, width, and depth separately, each with their own separate thresholds. Neural release system 70 may also or alternatively use ratios, such as the ration of foramen height to disc height, again with its own separate threshold.

Figure 2A:
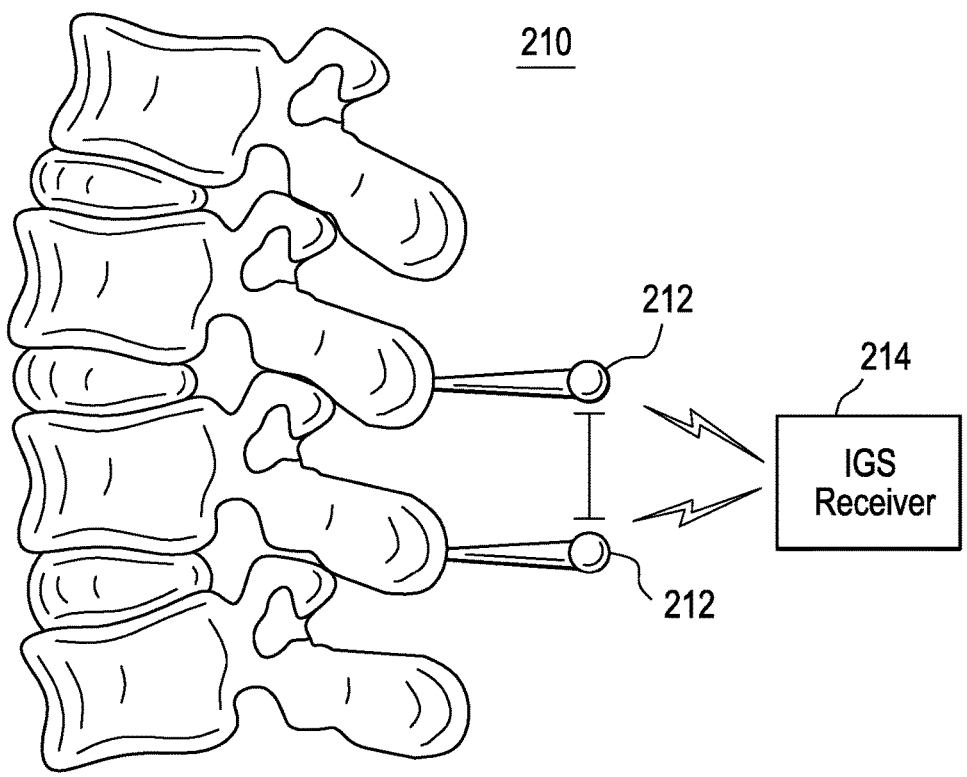

Neural spacing monitoring system 72 may be implemented in a variety of embodiments. For example, neural spacing monitoring system 72 may be an image guided surgery system 210. As shown in FIG. 2a, image guided surgery system 210 includes markers 212 which are placed on the spinal column at known defined locations with a known defined relationship to the spinal column structure. Image guided surgery system 210 also includes an image guided surgery system receiver 214 that receives signals from markers 212. Image guided surgery system 210 processes the signals and calculates the spatial position of markers. Image guided surgery system 210 determines an estimated model of the spine based on the spatial position of the markers and the pre-operative planning information which is representative of the structure of the spine. Image guided surgery system 210 then determines information representative of the existing neural foramen spacing prior to insertion of an implant which can be used as a baseline (instead of the pre-operatively estimated amount of neural compression) based on the estimated model of the spine and the locations of the markers.

Figure 2B:
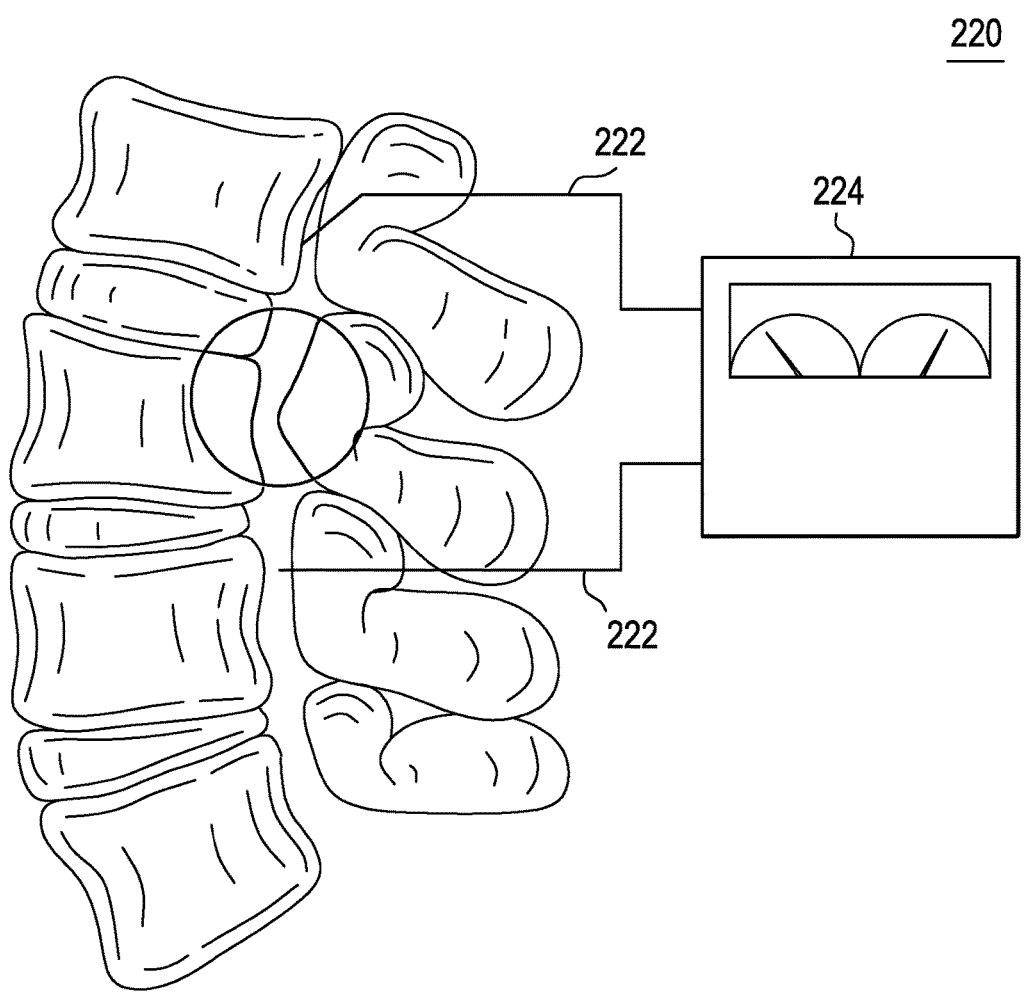

Neural spacing monitoring system 72 may be a pressure system 220. As shown in FIG. 2b, pressure system 220 includes pressure sensors 222 which are placed on the spinal column on opposite sides of neural compression. Pressure system 220 also includes a receiver 224 that receives signals from pressure sensors 222. Pressure system 220 processes the signals and calculates the pressure differential across the neural compression. The pressure differential can be used as information representative of the neural foramen spacing prior to insertion of an implant which can be used as a baseline (e.g., a smaller differential represents a larger foramen spacing). Pressure system 220 may also monitor local epidural pressure changes and/or pressure pulses or waves to intraoperatively detect the amount of neural release.

Neural spacing monitoring system 72 may be a direct visualization system 230. As shown in FIG. 2c, direct visualization system 230 includes a steerable camera 232 which is placed in an instrument 236. Instrument 236 has a proximal end including camera steering controls (not shown) and a distal end including a steerable camera. The distal end of the instrument 236 is designed with open areas for access to visualizing the spine. As shown, instrument 236 includes a relatively flat upper portion 231a configured to abut a superior vertebral body and a relatively flat lower portion 231b configured to abut an inferior vertebral body (alternatively the upper and lower portions may be shaped with a curve designed to match the shape of an average vertebral body endplate). The spacing between the upper portion 231a and the lower portion 231b is comparable to the height of the disc space. Multiple instruments may be provided with different spacing to accommodate various disc space heights. The upper portion 231a and lower portion 23b may be tapered or chamfered to facilitate movement within the disc space. The upper portion 231a and lower portion 231b are interconnected by walls 233. Walls 233 are typically narrow to increase viewing area.

Direct visualization system 230 also includes an image guided surgery system receiver 234 that receives signals from camera 232. Direct visualization system 230 determines an estimated model of the spine based on the signal from the camera and the pre-operative planning information which is representative of the structure of the spine. Direct visualization system 230 further determines information representative of the neural foramen spacing based on the video signals and the pre-operative model of the spine. This may be used as a baseline by neural release system 72 instead of the pre-operatively estimated amount of neural compression.

Figure 2D:
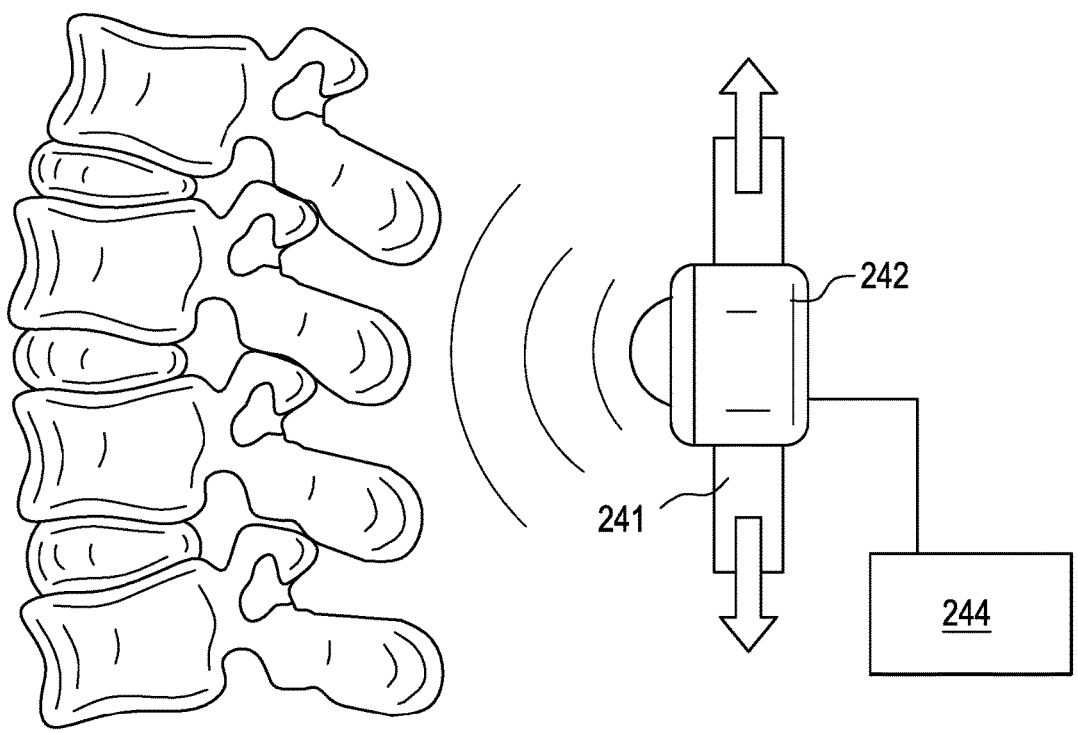

Neural spacing monitoring system 72 may be an ultrasonic detection system 240. As shown in FIG. 2*d,* ultrasonic detection system 230 includes an ultrasonic probe 242. Ultrasonic probe 242 is positioned on railing 241 to provide controlled movement of probe 242. Ultrasonic probe may also be handheld or controlled by various other motion control systems. Ultrasonic detection system 240 also includes an ultrasonic receiver 244 that receives signals from ultrasonic probe 242. Ultrasonic detection system 240 determines an estimated model of the spine based on the signal from ultrasonic probe 242 and the pre-operative planning information representative of the structure of the spine. Ultrasonic detection system 240 further determines information representative of the neural foramen spacing based on the ultrasonic probe 242 and the pre-operative model of the spine. This may be used as a baseline by neural release system 72 instead of the pre-operatively estimated amount of neural compression.

Neural spacing monitoring system 72 may be a conformable balloon system 250. As shown in FIG. 2*e,* conformable balloon system 250 includes a conformable balloon 252. Conformable balloon system 250 also includes a pressure receiver 254 that receives signals from conformable balloon 252. Conformable balloon system 250 determines information representative of the neural foramen spacing based on the pressure in conformable balloon 252. This may be used as a baseline by neural release system 72 instead of the pre-operatively estimated amount of neural compression.

Figure 2F:
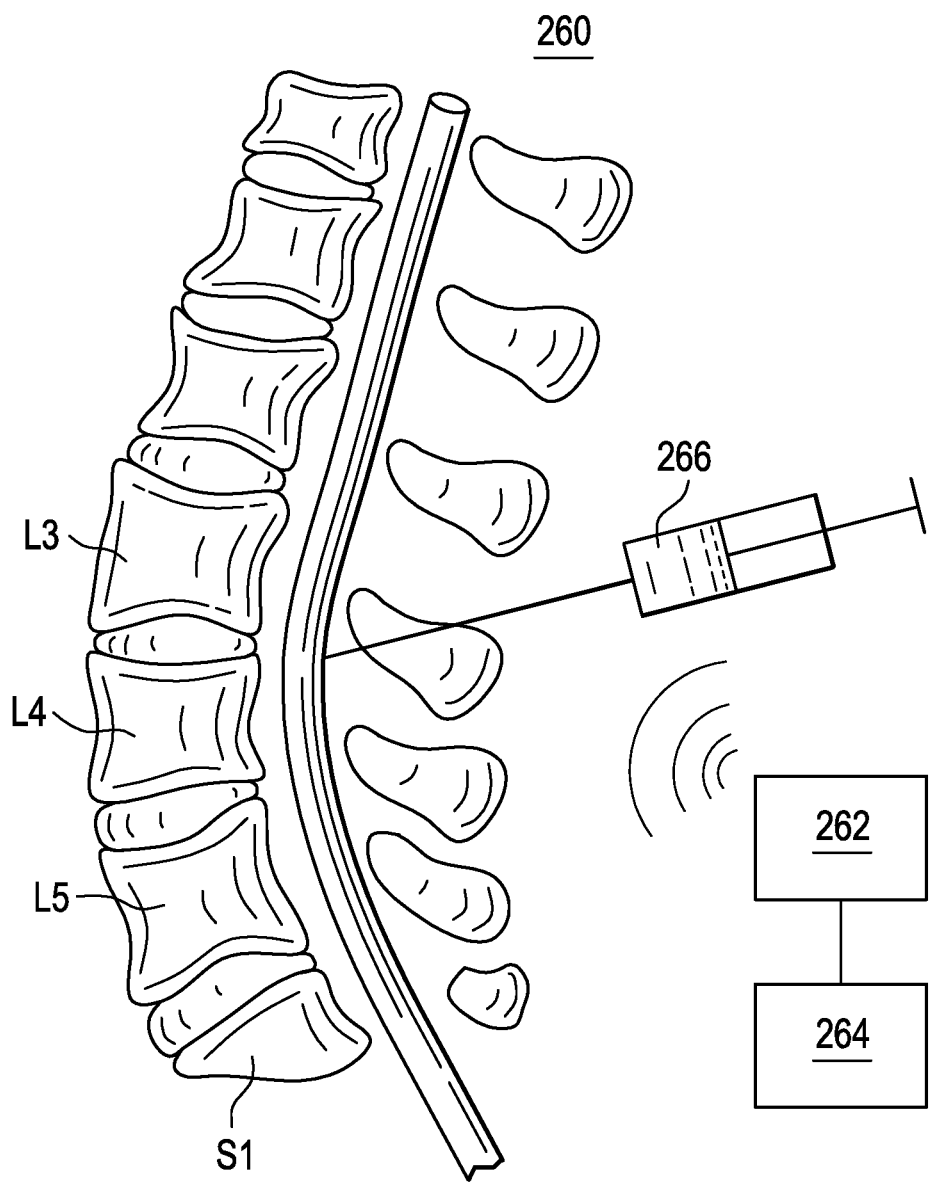

Neural spacing monitoring system 72 may be a mylogram system 260. As shown in FIG. 2*f,* mylogram system 260 includes a fluoroscope 262. Mylogram system 260 also includes a fluoroscopic receiver 264 that receives signals from fluoroscope 262. To improve the quality of the fluoroscopic signals, the patient may be injected with contrast agents to assist in determining neural compression and/or constrictions. Mylogram system 260 determines an estimated model of the spine based on the signal from fluoroscope 262 and the pre-operative planning information representative of the structure of the spine. Mylogram system 260 further determines information representative of the neural foramen spacing based on the fluoroscope 262 and the pre-operative model of the spine. This may be used as a baseline by neural release system 72 instead of the pre-operatively estimated amount of neural compression.

As shown at step 120, the surgeon performs initial disc cleaning. Disc cleaning is performed to make room for the fusion cage and to expose the endplates of the vertebral body which is believed to assist with the fusion process. The surgeon may also place a trial in the cleared disc space to get a tactile feel for how well the disc space has been cleared. The trial may also be used to determine whether a particular size implant will fit in the disc space.

Figure 3A:
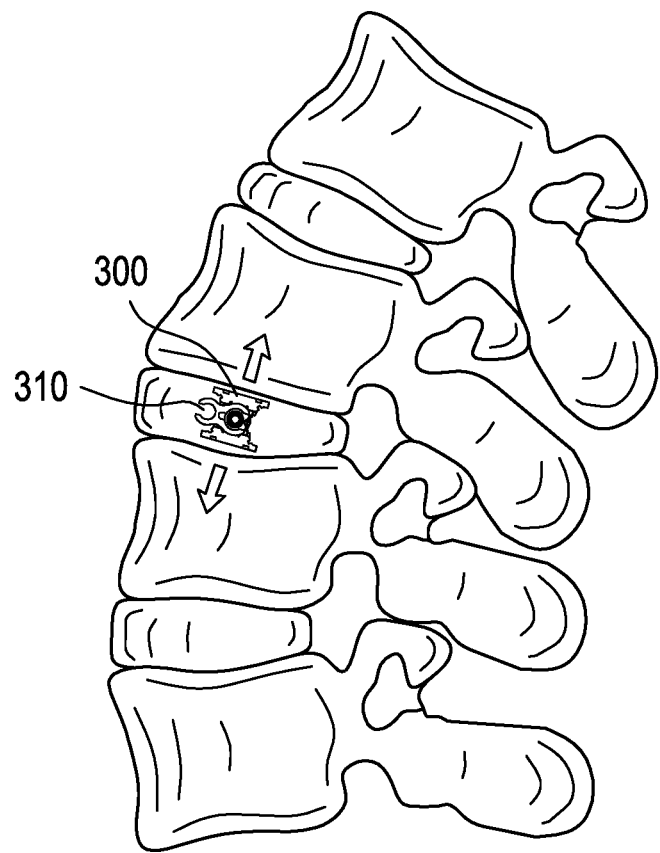

At step 130, the surgeon inserts and adjusts an expandable trial implant into the cleaned vertebral disc space while monitoring load and/or contact area. An exemplary expandable trial implant 300 for monitoring load and/or contact area is shown in FIG. 3*a.* As can be seen in FIG. 3*a,* the expandable trial implant 300 has recesses 310 located on the lateral sides of the implant. Recesses 310 allow the surgeon to insert additional disc cleaning tools to selectively remove more tissue near either or both of the lateral sides of the implant. Further, the surgeon may selectively remove tissue near the distal and/or proximal portions of the implant. Spinal correction system 50 can assist in determining which area of tissue to remove in order to achieve a planned amount of neural release.

The lateral sides of implant may access different portion of the disc depending on the type of procedure performed. For example, in a spinal procedure with lateral access, such as shown in FIG. 3*a,* the lateral sides of the trial implant would face the anterior and posterior portions of the disc. In a spinal procedure with anterior access, not shown, the lateral sides of the trial implant would face the anterior and posterior portions of the disc.

Figure 3B:
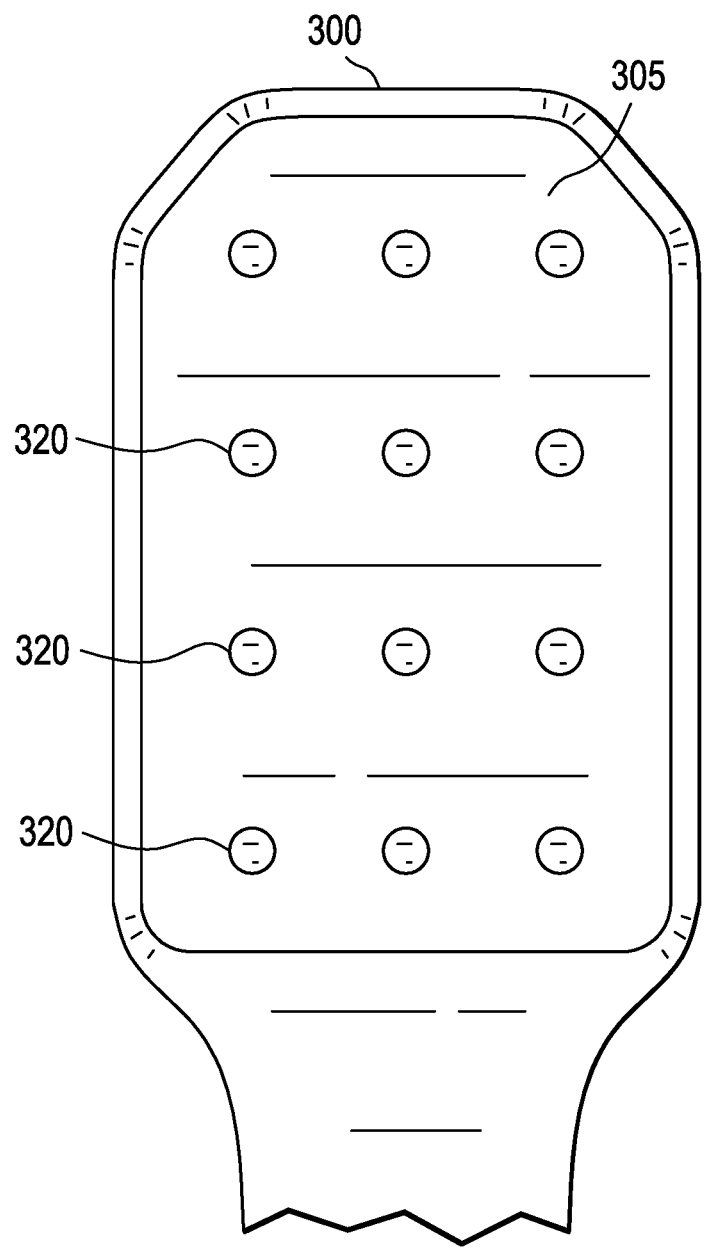

FIG. 3*b* is a top view of expandable trial implant 300. As shown in FIG. 3*b,* expandable trial implant 300 includes a relatively flat upper surface 305 configured to abut a superior vertebral body. Expandable trial implant 300 also includes a relatively flat lower surface (not shown) configured to abut an inferior vertebral body. Upper surface 305 and the lower surface may be tapered or contoured to conform to a typical vertebral body endplate. Upper surface 305 and the lower surface may be generally parallel to each other or may be angled in a generally kyphotic or generally lorditoc configuration, again to match typical vertebral body configurations.

As shown in FIG. 3*b,* upper surface 305 includes a plurality of load cells 320. The lower surface may also include a plurality of load cells (not shown). The load cell may be a pressure sensor, load cell, or any other device capable of sensing pressure or load. Load cells 320 are arranged on the top surface and disposed along the lateral sides of the expandable trial implant 300. Load cells 320 are also positioned near the proximal and distal ends of the implant. While the load cells 320 are shown as being positioned into rows and columns the load cells 320 may be located at various positions on upper surface 305 and the lower surface. The spacing of the loads cells may be uniform or may be more densely located in areas or more interest to the surgeon, e.g., the spacing may be more dense around the perimeter rather than in the central region of the upper and lower surfaces.

Load cells 320 communicate with load and contact system 65 to provide information about the load on expandable trial implant 300 as it is being expanded. Load and contact system 65 may determine whether and when contact is made with the vertebral bodies. Load and contact system 65 may interpret a load greater than some threshold load as an indication that contact has been made with the vertebral bodies. Load and contact system 65 may indicate to the surgeon when contact occurs (visually, audibly, or both, and may be done via neural release system 70 and display 74).

Alternatively, the upper surface 305 and lower surface may include contact switches or sensors to signal when contact with the vertebral bodies is made. Upper surface 305 and lower surface may alternatively include a film or sheet of sensors for determining contact area/load at various locations on the upper and lower surfaces.

Figure 4A:
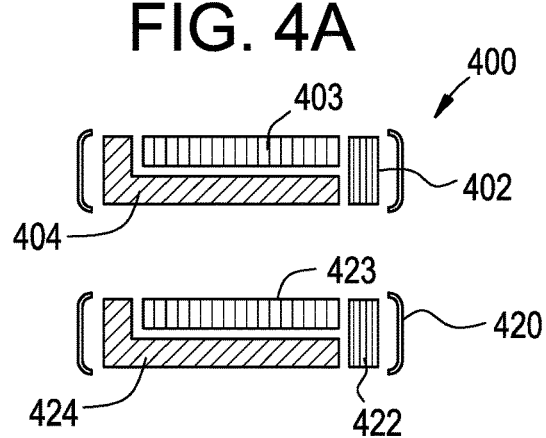
Figure 4B:
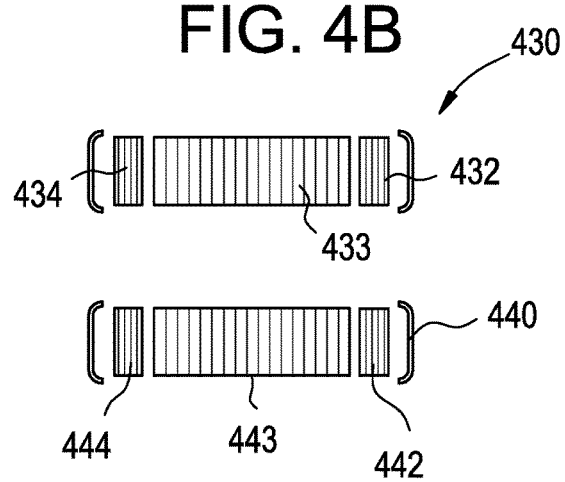
Figure 4C:
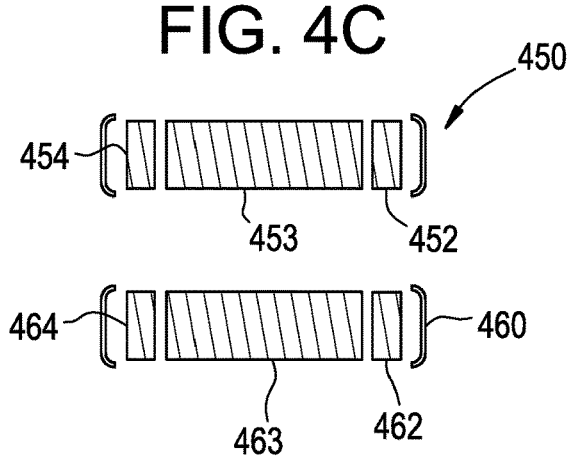

FIGS. 4*a* through 4*c* show exemplary embodiments of how display 74 may illustrate the load and contact on the expandable trial implant 300. As shown in FIG. 4*a,* graphical view 400 (which may be generated by load and contact system 65 and/or neural release system 70 and displayed on display 74) illustrates the load and contact on the superior surface of expandable trial implant 300. As shown in graphical view 420, region 402 is indicating a high load, region 403 is indicating a medium load, and region 404 is indicating a low load. The indications can be implemented with color, values, colors and values, may include the ability to zoom in and out of the graphical display for more or less resolution, etc. The load on the inferior surface of expandable trial implant 300 is also illustrated in view 420. As shown, region 422 is indicating a high load, region 423 is indicating a medium load, and region 424 is indicating a low load.

As shown in FIG. 4b, graphical view 430 illustrates the load on the superior surface of expandable trial implant 300. As shown in graphical view 430, region 432 is indicating a high load, region 433 is indicating a medium load, and region 434 is indicating a high load. The load on the inferior surface of expandable trial implant 300 is also illustrated in view 440. As shown, region 442 is indicating a high load, region 443 is indicating a medium load, and region 444 is indicating a high load.

As shown in FIG. 4c, graphical view 450 illustrates the load on the superior surface of expandable trial implant 300. As shown in graphical view 450, region 452 is indicating a low load, region 453 is indicating a low load, and region 454 is indicating a low load. The load on the inferior surface of expandable trial implant 300 is also illustrated in view 460. As shown, region 462 is indicating a low load, region 463 is indicating a low load, and region 464 is indicating a low load.

Still at step 130, the surgeon expands the expandable trial implant 300 but stops before the load increases over a predefined threshold which may be for example, a threshold that has been shown to allow for damage to the endplates. Neural release system 70 receives information from load and contact system 65 representing the load and contact area on the superior and inferior surfaces of expandable trial implant 300.

Neural release system 70 may signal, via display 74, when contact first occurs between the superior and inferior surfaces of expandable trial implant 300 contacts the endplates of the vertebral bodies. Neural release system 70 may also graphically display, via display 74, when each load cell on the superior and inferior surfaces of expandable trial implant 300 contacts the endplates of the vertebral bodies. Neural release system 70 may also signal, via display 74, when each of the four corners of the superior and inferior surfaces of expandable trial implant 300 contacts the endplates of the vertebral bodies.

Neural release system 70 compares the load information to a predefined threshold. This threshold can warn the surgeon of possible impending endplate damage. The predefined threshold may be a single load threshold which applies to each load cell, may be an average load threshold representing an average of each of the load cells on one or both surfaces of the expandable trial implant 300, or the predefined threshold may be a combination of single thresholds and an average threshold either of which will trigger a signal to the surgeon. When the predefined threshold is met or exceeded, display 74 or neural release system 70 may visually and/or audibly signal to the surgeon.

At step 140, the surgeon measures the neural foramen release. The surgeon may do this with any of the various neural spacing monitoring systems 72 shown more specifically in FIGS. 2a through 2f. Neural spacing monitoring systems 72 sends information to neural release system 70 for processing. If neural release system 70 determines that the measured neural foramen release is equal to or greater than the planned neural foramen release, then at step 150, neural release system 70 signals, via display 74, that the foramen is sufficiently released and the surgeon proceeds to step 170 and places the fusion implant into the disc space. Exemplary algorithms for determining whether the desired or planned neural release have been achieved were discussed above.

If neural release system 70 determines that the measured neural foramen release has not reached the planned neural foramen release, then at step 150, neural release system 70 signals that the foramen is not yet sufficiently released and the surgeon proceeds to step 160 and cleans more disc space based on the feedback provided by neural release system 70 and load and contact system 65. Neural release system 70 may indicate to the surgeon which areas of the disc should be further cleaned. Neural release system 70 may determine the areas based on the measured amount of neural release and the measured loads on expandable trial implant 300, as well as based upon a determined correlation between the changes in measured load and the resultant change in measured neural release. The correlation may be determined for a single patient, may be based on historical data on multiple patients (e.g., from data aggregation system 80), or combinations of both. The neural release system 70 may provide a graphical indication to the surgeon of where to remove more tissue from the disc space, similar to those in FIGS. 4a through 4c. As an example, the neural release system 70 may graphically show a vertebral body from a superior view, from a lateral view, and from an anterior view and indicate with color from which regions of the disc, the surgeon should remove more tissue to achieve the planned neural release.

After completing step 160, the method 10 proceeds back to step 130 in which the surgeon will again place the expandable trial implant 300 in the disc space and expand the trial while monitoring the load and contact area. This process is repeated until the planned amount of neural foramen release is achieved, or until other limits are reached such as a maximum amount of disc space retraction, a maximum operative time, measurements of nerve distress, or other such items (not shown in the flow chart).

FIGS. 5a through 5h show an exemplary embodiment another expandable trial implant 500 which may be used in connection with the method of FIG. 1a instead of or in combination with expandable trial implant 300. Expandable trial implant 500 includes a superior portion 510, an inferior portion 530, and an expansion portion 550 located between the superior portion 510 and inferior portion 530.

Superior portion 510 is shaped generally rectangular with an upper surface 511 that is generally flat (but may be shaped generally convexly or otherwise shaped and configured to mate with a typically shaped vertebral body endplate) and is configured to contact a superiorly positioned vertebral body. Superior portion 510 includes load cells 502 located on the upper surface 511.

Superior portion 510 includes a distal portion 514 and a proximal portion 515. The distal portion 514 of superior portion 510 may be tapered and/or chamfered to allow easier insertion into the disc space. The proximal portion 515 of superior portion 510 may also be tapered and/or chamfered to allow easier removal from the disc space and would typically be less tapered/chamfered that the distal portion 514.

Inferior portion 530 is shaped generally rectangular with a lower surface 531 that is generally flat (but may be shaped generally convexly or otherwise shaped and configured to mate with a typically shaped vertebral body endplate) and is configured to contact an inferiorly positioned vertebral body. Inferior portion 530 includes load cells 502 located on the lower surface 531.

Superior portion 530 includes a distal portion 534 and a proximal portion 535. The distal portion 534 of superior portion 530 may be tapered and/or chamfered to allow easier insertion into the disc space. The proximal portion 535 of superior portion 530 may also be tapered and/or chamfered to allow easier removal from the disc space and would typically be less tapered/chamfered that the distal portion 534.

Superior portion 510 includes lateral side walls 520 extending generally downward from upper surface 511 and between the distal portion 514 and proximal portion 515. Inferior portion 530 includes lateral side walls 540 extending generally upward from lower surface 531 and between the distal portion 534 and proximal portion 535.

Figure 5A:
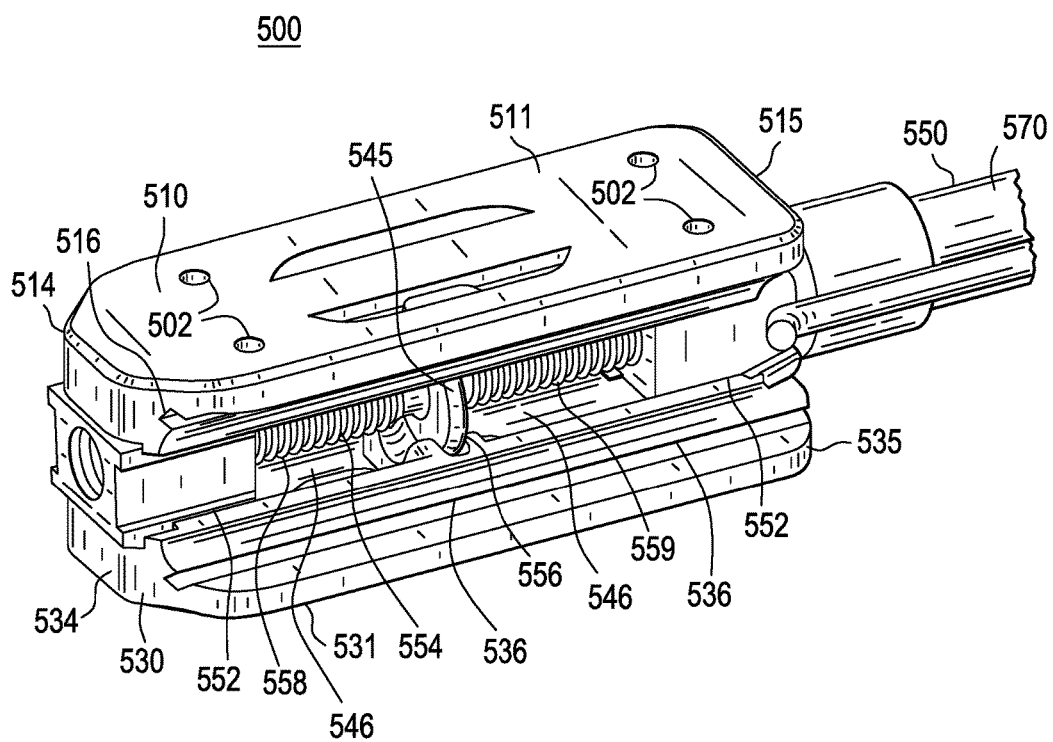
Figure 5B:
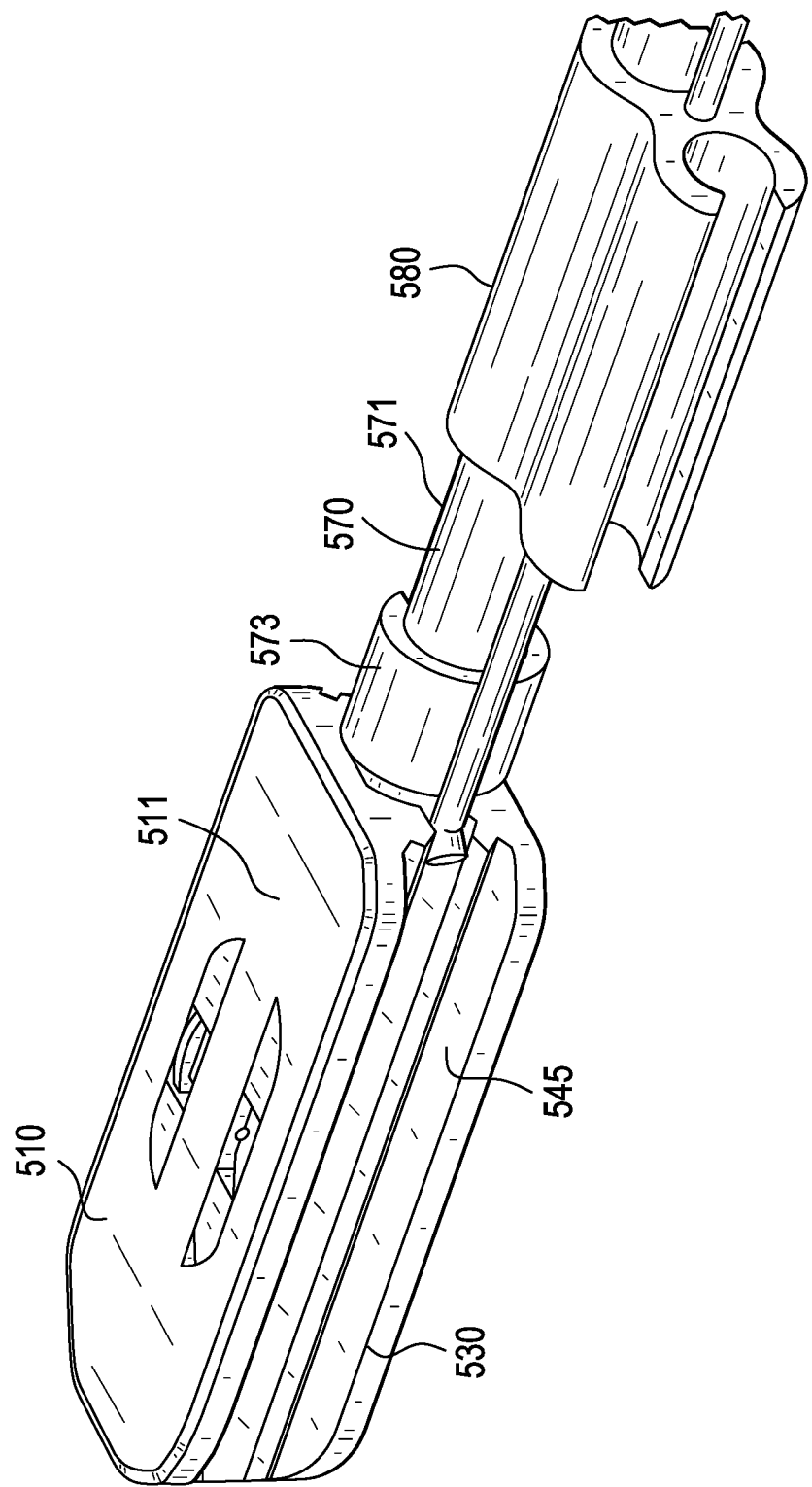
Figure 5C:
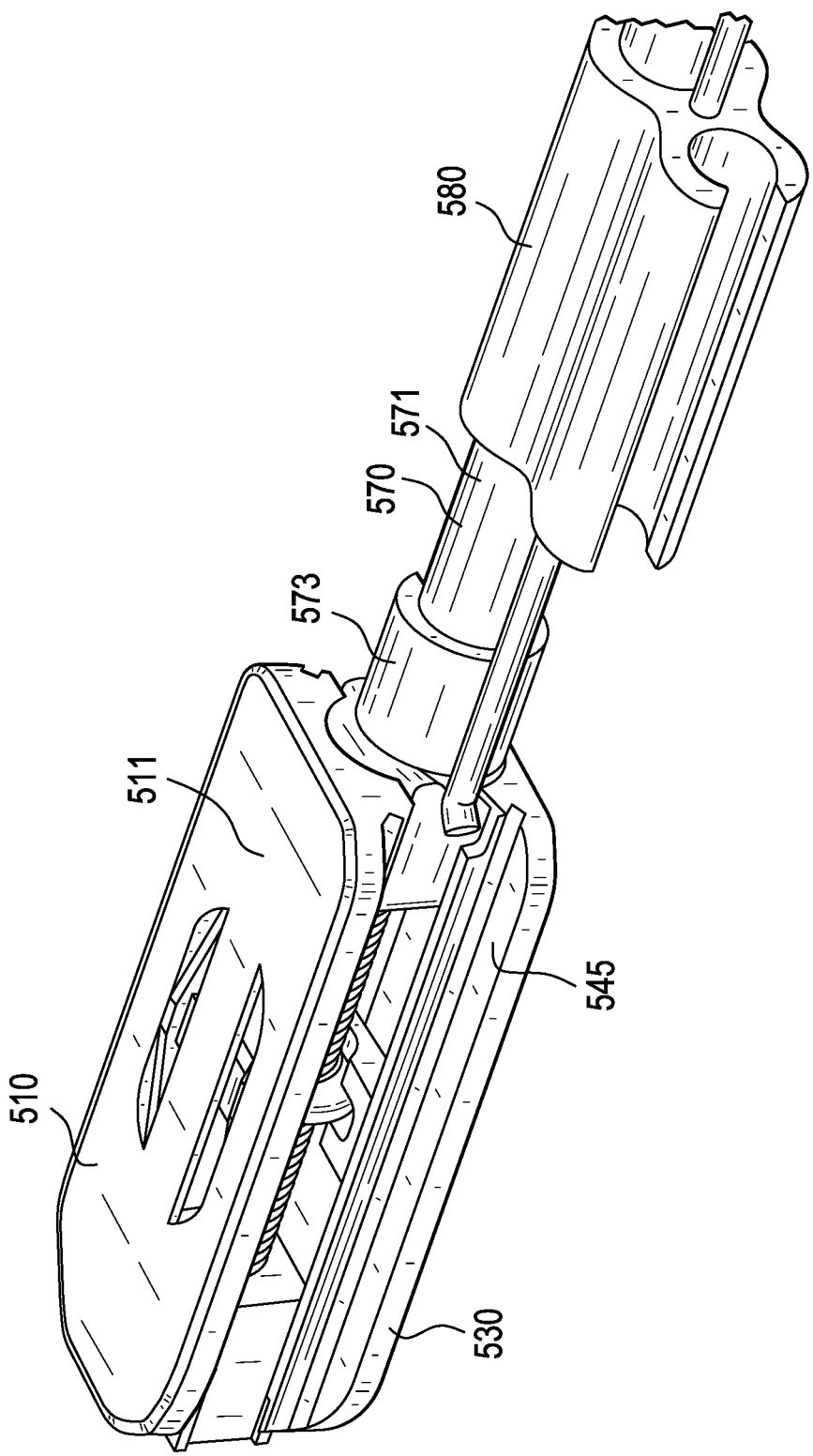
Figure 5D:
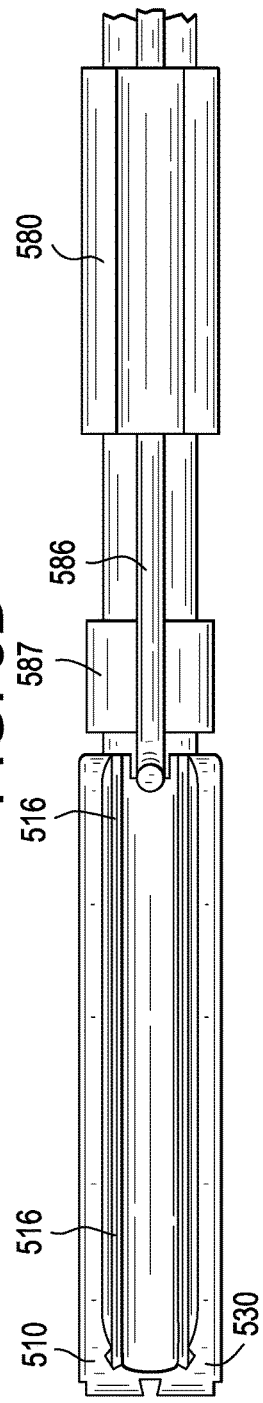
Figure 5E:
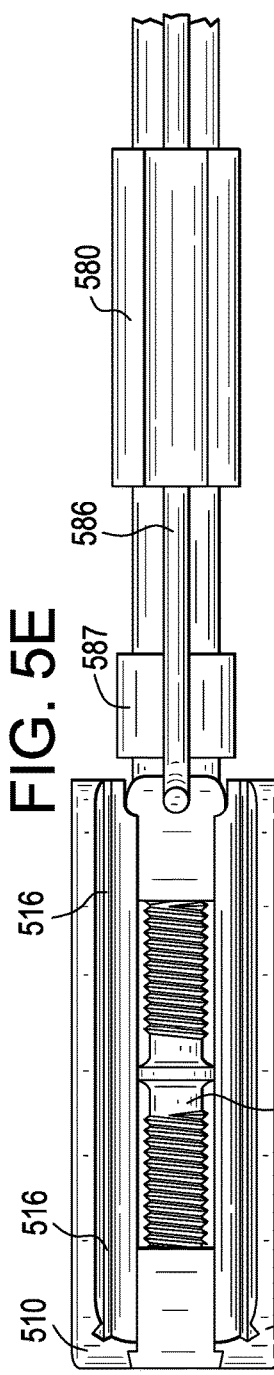
Figure 5F:
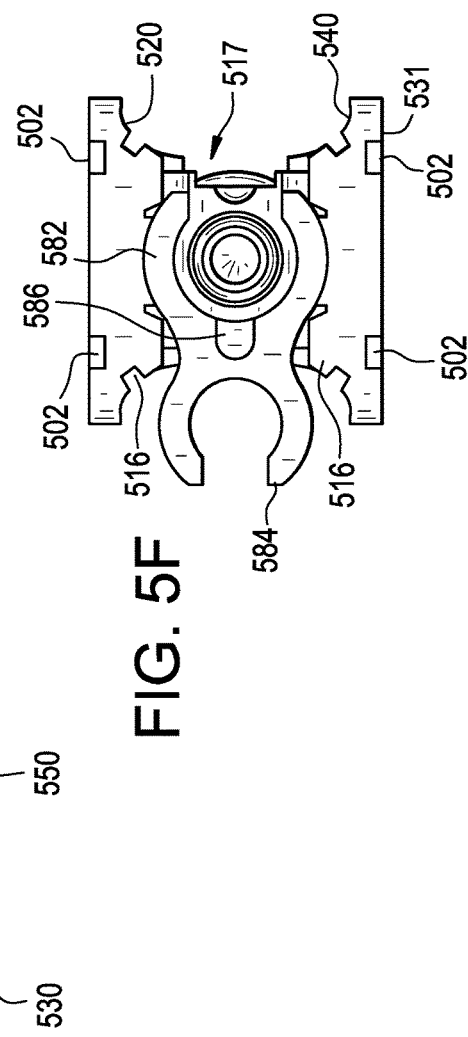
Figure 5G:
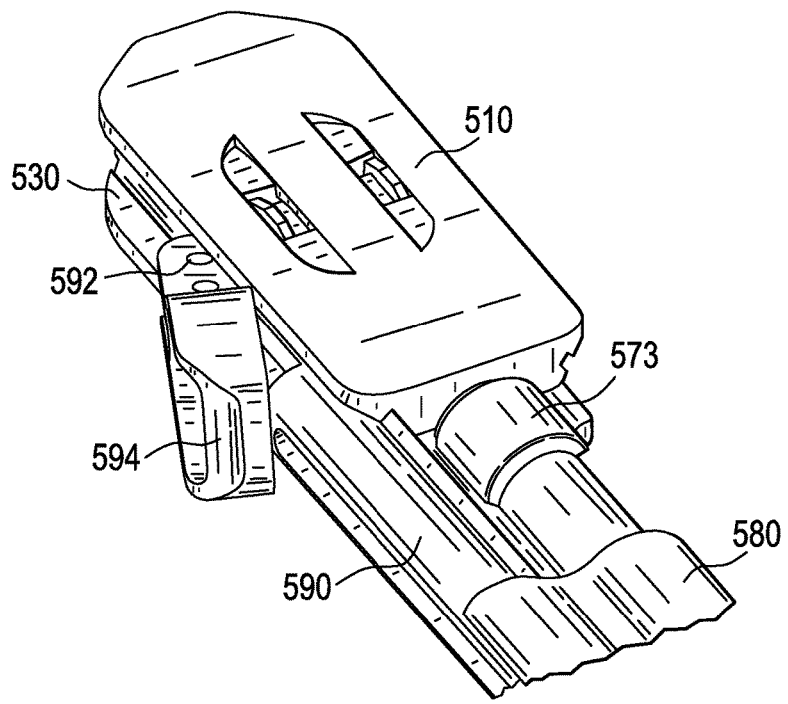

Rather than being generally flat, side walls 520, 540 include a concavely shaped section and together form a C-shape in the lateral portion of expandable trial implant 500, as best seen in the view of FIG. 5f. This C-shape provides an area 517 on each side of the implant for inserting and using a disc cleaning tool. While expandable trial implant 500 includes generally mirror image and symmetric superior portion 510 and inferior portion 530, implant 500 may also be non-symmetric. Further, it is not mandatory that each side wall include a concavely shaped section; the concavity may be included only on one portion. Moreover, the concavely shaped section may be any shape that provides a recessed area for a disc removal tool (described in more detail below), such as a rectangular recess, a square recess, or other shapes.

Side wall 520 includes a groove 516 extending from the proximal portion 515 to the distal portion 514 (although groove 516 does not have to extend all the way to the distal portion 514). Side wall 540 also includes a groove 516 extending from the proximal portion 535 to the distal portion 534 (although groove 536 does not have to extend all the way to the distal portion 534). Groove 516 has a rectangular cross section and is sized and configured to mate with a portion of a disc clearing tool to guide and retain the disc clearing tool, described in more detail below. While groove 516 is shown with a rectangular cross section, the cross section may have various shapes to mate with the disc clearing tool, such as a circular shape, square shape, dovetail shape, etc.

Expansion portion 550, which is disposed between superior portion 510 and inferior portion 530, includes a threaded rod portion 554, two wedges 552 (that are internally threaded and mate with the threads of rod portion 554), and a shaft portion 570 connected to rod portion 554 to rotate rod portion 554. As shaft portion 570 is rotated, threaded rod portion 554 is also rotated. Expansion portion can also be comprised of other mechanisms for expansion, including balloons, pistons, jacks, shims, etc.

Threaded rod portion 554 includes a central circular flange 556 and two oppositely threaded portions 558 and 559 on either side of central flange. Central flange 556 mates with arcuate recesses 525, 545 located on the lower side of superior portion 510 and the upper side of inferior portion 530, respectively. Rotation of threaded rod portion 554 causes wedges 552 to move in opposite directions, i.e., either towards each other or away from each other. As wedge 552 move toward each other, they move along ramps located on the lower side of superior portion 510 and the upper side of inferior portion 530, causing superior portion 510 and inferior portion 530 to expand apart.

Shaft portion 570 includes a driving shaft 571, an implant mating portion 573, and a tool guide portion 580. As best seen in FIG. 5f, tool guide portion 580 includes a shaft mating section 582 and a tool mating section 584. Shaft mating section 582 extends longitudinally along driving shaft 571 and has a C-shaped cross-section that is sized and configured to snap onto driving shaft 571. Tool mating section 584 extends longitudinally along shaft mating section 582 and has a C-shaped cross-section that is sized and configured to mate with a disc clearing tool. Shaft portion 570 further includes a camera 586 located between shaft mating section 582 and a tool mating section 584. Camera 586 is in electrical communication with either load and contact system 65 or neural release system 70 which in turn provides information to display 74 to show camera images of the disc space and assist the surgeon with disc removal.

Expandable trial implant 500 may mechanically cooperate with a disc removal tool 590 to allow the surgeon to remove sections of the disc. This can occur, for example, after determination by neural release system 70 that a particular region of disc should be removed, as described above.

Disc removal tool 590 includes a shaft 591 and a cutting implement 594. Cutting implement 594 is shown as a box cutter having four walls forming a square with rounded corners and an aperture therethrough. The walls have sharp edges to cut disc material. Cutting implement 594 may take the shape of any other conventional cutting implement commonly used for disc cutting or removal.

Cutting implement 594 is pivotably connected to shaft 591 at hinge 592. Hinge 592 allows cutting implement 594 to articulate about a pivot point and cut disc from the disc space. Cutting implement 594 can be articulated by interconnected driving shafts or pulleys or any other conventional methods for mechanically producing a pivoting movement. Disc removal tool 590 includes a handle (not shown) and a trigger mechanism (not shown) for the surgeon to control the articulation angle when removing disc material. Cutting implement 594 may also be non-articulating cutting element that is sized and configured to be mate with expandable trial implant 500 described in more detail below.

Figure 5H:
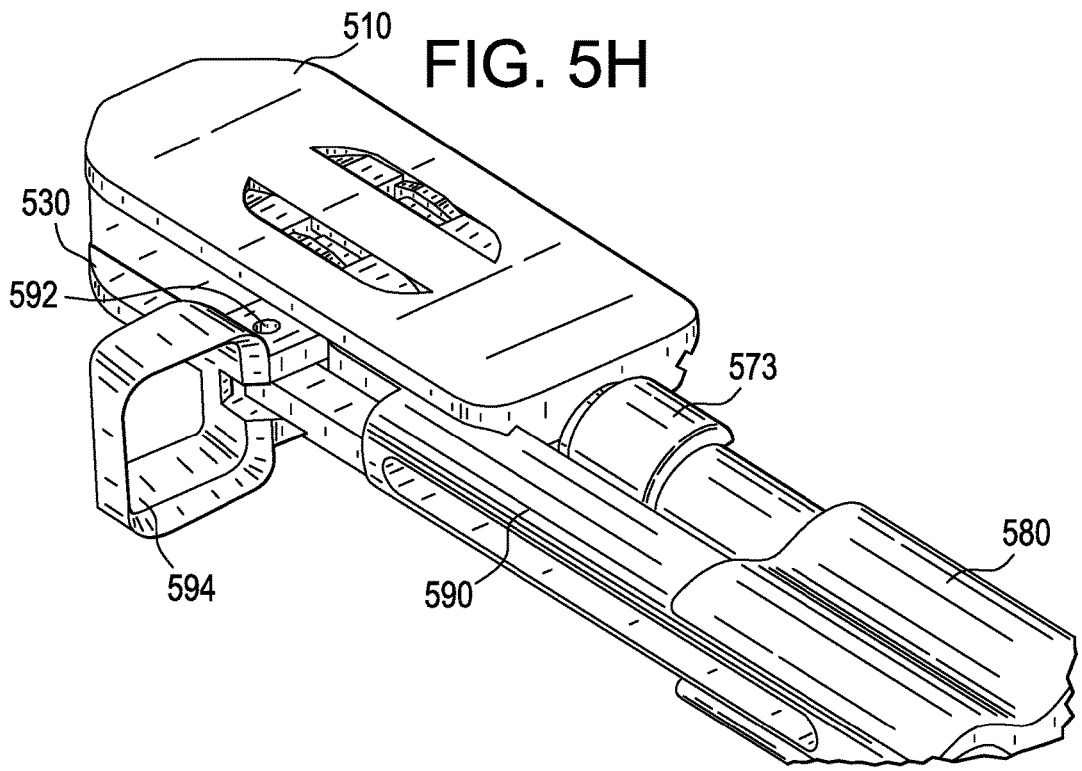

Shaft 591 of disc removal tool 590 is disposed in the C-shaped cross-section of the tool mating section 584 of expandable trial implant 500, as seen in FIG. 5h. This allows disc removal tool 590 to move longitudinally with respect to expandable trial implant 500. Shaft 591 includes a longitudinal projection 596 extending along the length of shaft 591. As shown, longitudinal projection 596 is generally rectangular in cross-section and is sized and configured to mate with and be received in groove 516 in the lateral recess 545 of expandable trial implant 500. The mating between stabilizes the disc removal tool 590 by limiting the motion of shaft 591 to longitudinal motion and preventing rotational movement. This may provide the surgeon with added stability to assist with removal of disc material. Alternatively, the shaft 591 may not include longitudinal projection 596, thereby allowing the surgeon the ability to rotate the shaft 591 when appropriate. A kit may be provided with multiple cutting implements, each provided with and without longitudinal projection 596, thereby providing the surgeon the option of increased stability when appropriate and increased flexibility when appropriate.

FIGS. 6a through 6h show an alternative exemplary embodiment of an expandable trial implant 600 which may be used in connection with the method of FIG. 1a instead of or in combination with expandable trial implant 300 or expandable trial implant 500. Expandable trial implant 600 includes a superior portion 610, an inferior portion 630, and an expansion portion 650 located between the superior portion 610 and inferior portion 630.

Superior portion 610 is shaped generally rectangular with an upper surface 511 that is generally flat (but may be shaped generally convexly or otherwise shaped and configured to mate with a typically shaped vertebral body endplate) and is configured to contact a superiorly positioned vertebral body. Superior portion 610 includes load cells 602 located on the upper surface 611.

Superior portion 610 includes a distal portion 614 and a proximal portion 615. The distal portion 614 of superior portion 610 may be tapered and/or chamfered to allow easier insertion into the disc space. The proximal portion 615 of superior portion 610 may also be tapered and/or chamfered to allow easier removal from the disc space and would typically be less tapered/chamfered that the distal portion 614.

Inferior portion 630 is shaped generally rectangular with a lower surface 631 that is generally flat (but may be shaped generally convexly or otherwise shaped and configured to mate with a typically shaped vertebral body endplate) and is configured to contact an inferiorly positioned vertebral body. Inferior portion 630 includes load cells 602 located on the lower surface 631.

Superior portion 630 includes a distal portion 634 and a proximal portion 635. The distal portion 634 of superior portion 630 may be tapered and/or chamfered to allow easier insertion into the disc space. The proximal portion 635 of superior portion 630 may also be tapered and/or chamfered to allow easier removal from the disc space and would typically be less tapered/chamfered that the distal portion 634.

Superior portion 610 includes lateral side walls 620 extending generally downward from upper surface 611 and between the distal portion 614 and proximal portion 615. Inferior portion 630 includes lateral side walls 640 extending generally upward from lower surface 631 and between the distal portion 634 and proximal portion 635.

Figure 6A:
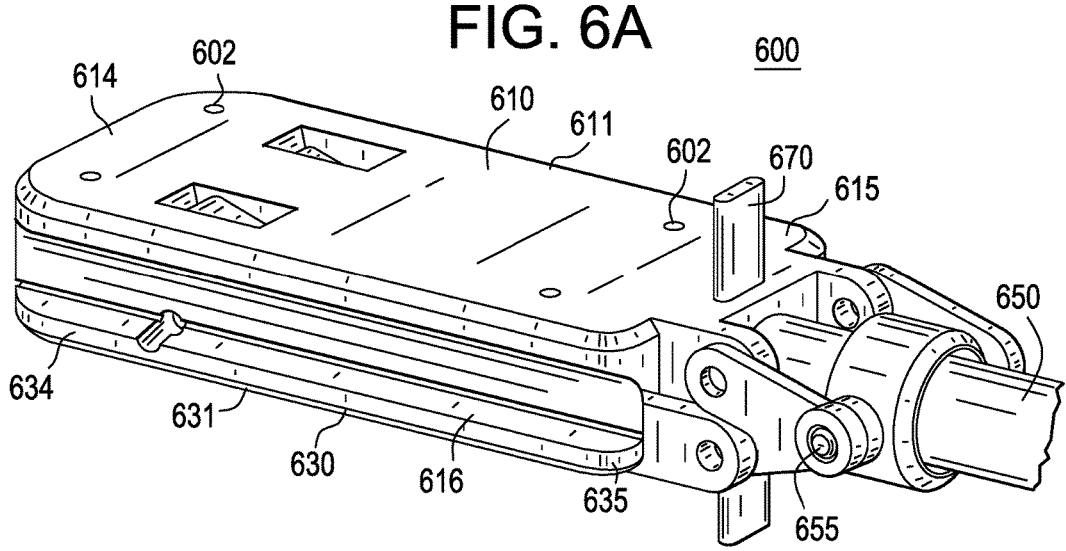
Figure 6B:
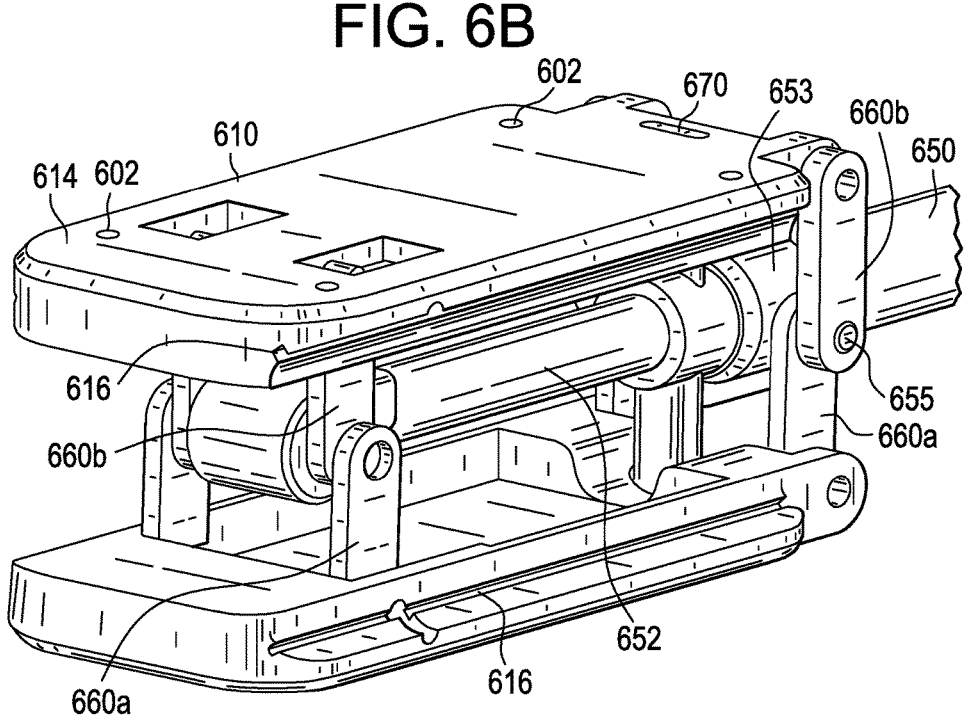
Figure 6C:
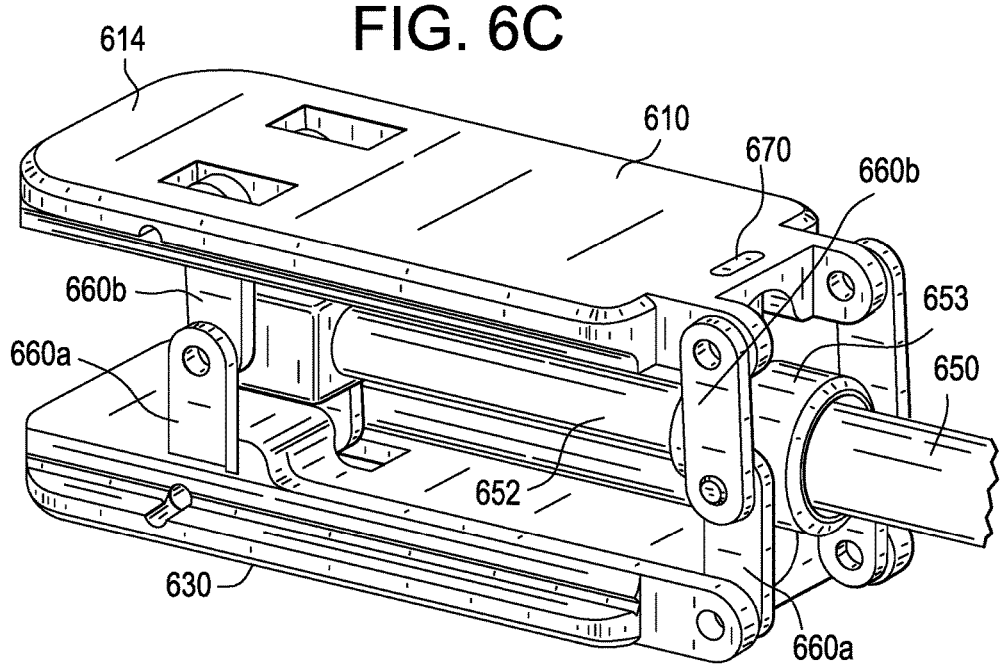
Figure 6D:
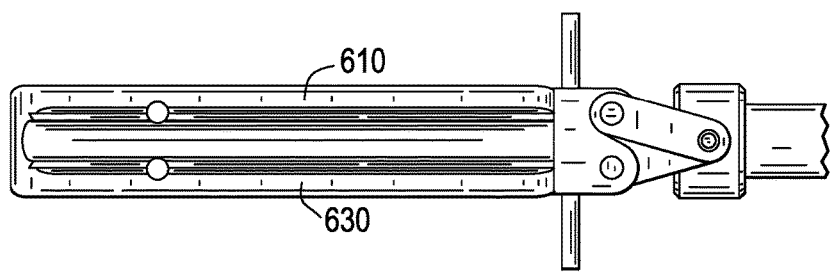
Figure 6E:
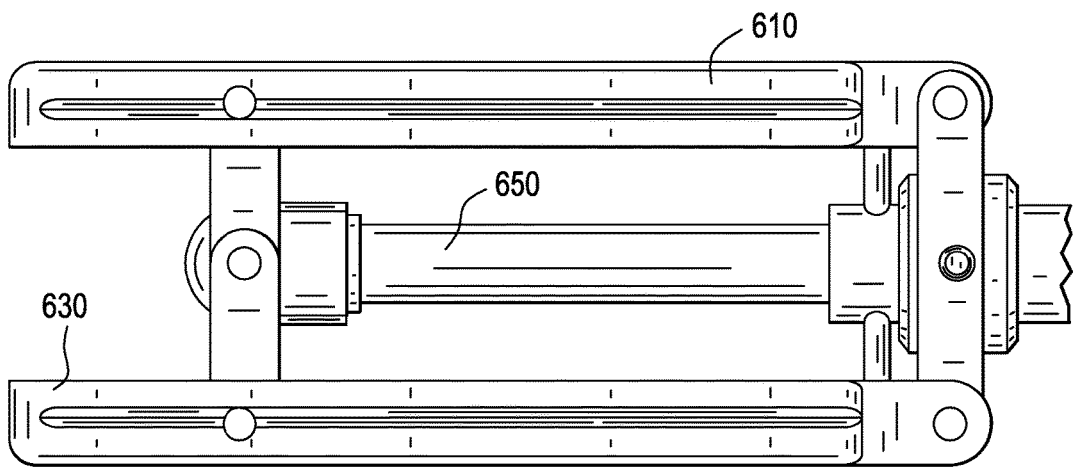
Figure 6F:
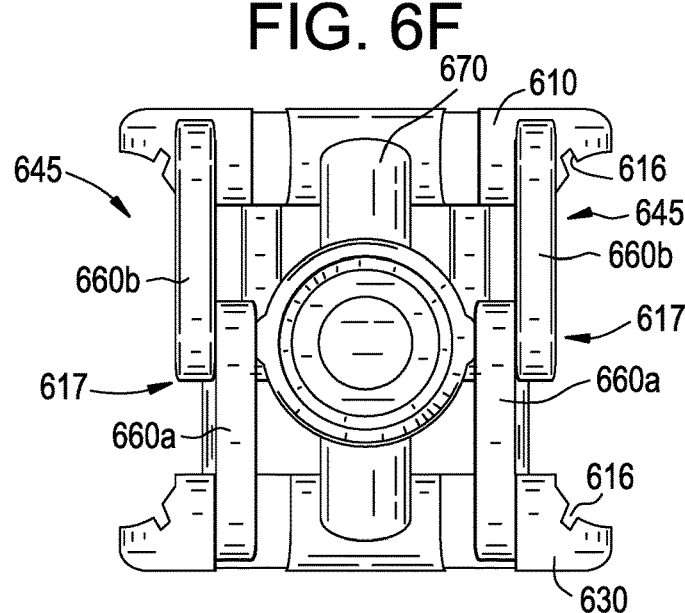
Figure 6G:
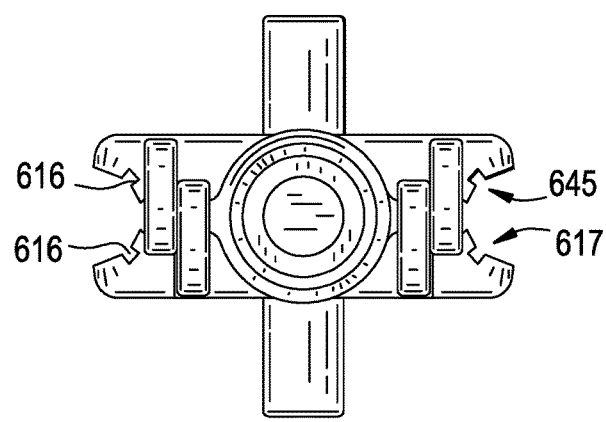
Figure 6H:
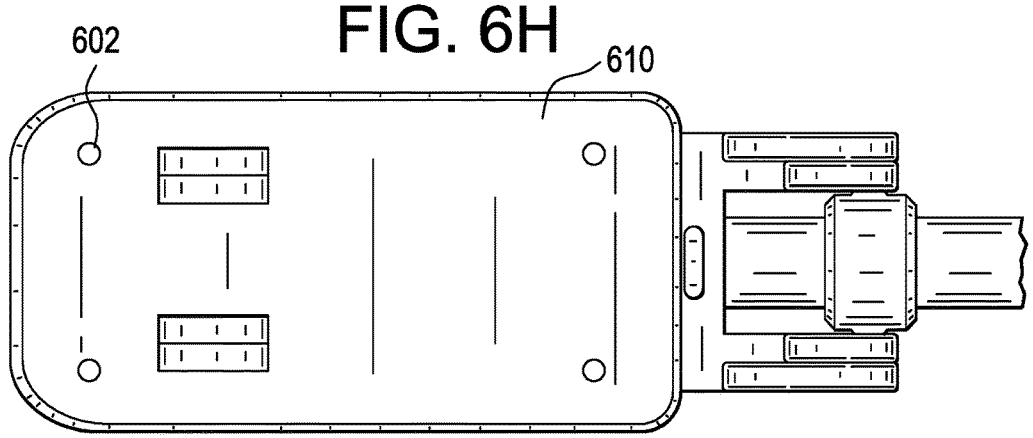

Rather than being generally flat, side walls 620, 640 include a concavely shaped section and together form a C-shape in the lateral portion of expandable trial implant 600, as best seen in the view of FIG. 6g. This C-shape provides an area 617 on each side of the implant for inserting and using a disc cleaning tool. While expandable trial implant 600 includes generally mirror image and symmetric superior portion 610 and inferior portion 630, implant 600 may also be non-symmetric. Further, it is not mandatory that each side wall include a concavely shaped section; the concavity may be included only on one portion. Moreover, the concavely shaped section may be any shape that provides a recessed area for a disc removal tool (described in more detail below), such as a rectangular recess, a square recess, or other shapes.

Side wall 620 includes a groove 616 extending from the proximal portion 615 to the distal portion 614 (although groove 616 does not have to extend all the way to the distal portion 614). Side wall 640 also includes a groove 616 extending from the proximal portion 635 to the distal portion 634 (although groove 636 does not have to extend all the way to the distal portion 634). Groove 616 has a rectangular cross section and is sized and configured to mate with a portion of a disc clearing tool to guide and retain the disc clearing tool, described in more detail below. While groove 616 is shown with a rectangular cross section, the cross section may have various shapes to mate with the disc clearing tool, such as a circular shape, square shape, dovetail shape, etc.

Expansion portion 650, which is disposed between superior portion 610 and inferior portion 630, includes a distal hinge 651 and a proximal hinge 653 connected by a longitudinal member 652. Distal hinge 651 is shaped generally as a square but could take any shape and includes two lateral projections 655 extending laterally from opposite sides of the distal hinge 651. Proximal hinge 653 is shaped generally annular and is disposed around rod 654. Proximal hinge 653 includes two lateral projections 655 extending laterally from opposite portions of the proximal hinge 653.

Expansion portion 650 is linked to superior portion 610 and inferior portion 630 by a series of four jacks 660 although there could be any number of jacks 660. As shown in FIG. 6c, each jack 660 includes at least two longitudinal members shown as 660a and 660b pivotally interconnected to each other at a pivot point and to the projection 655 of distal hinge 651 (or the projection 655 of proximal hinge 653).

Rod 654 extends from a handle (not shown) towards and through proximal hinge 653. Rod 654 culminates with two extension flanges 670. A first extension flange 670 extends upwards toward and through a recess of superior portion 610. A second extension flange 670 extends downward toward and through a recess of inferior portion 630. The extension flanges 670 may also function as an over-insertion stop, stopping the surgeon from over-inserting the expandable trial implant 600 too far into the disc space.

As proximal hinge 653 is pushed longitudinally with respect to rod 654, jacks 660 are forced to pivot moving the expandable trial implant 600 from the compressed position (such as shown in FIG. 6a) and into the expanded position (such as shown in FIGS. 6b and 6c.

As with expandable trial implant 500, expandable trial implant 600 may include a tool guide portion 580 as shown in FIGS. 5b and 5c. Shaft 591 of disc removal tool 590 is disposed in the C-shaped cross-section of the tool mating section 584 of expandable trial implant 600 (not shown). This allows disc removal tool 590 to move longitudinally with respect to expandable trial implant 600. Shaft 591 includes a longitudinal projection 596 extending along the length of shaft 591. As shown, longitudinal projection 596 is generally rectangular in cross-section and is sized and configured to mate with and be received in groove 616 in the lateral recess 645 of expandable trial implant 600. The mating between stabilizes the disc removal tool 590 by limiting the motion of shaft 591 to longitudinal motion and preventing rotational movement. This may provide the surgeon with added stability to assist with removal of disc material. Alternatively, the shaft 591 may not include longitudinal projection 596, thereby allowing the surgeon the ability to rotate the shaft 591 when appropriate.

The above described method can be implemented in a manual, step-wise fashion requiring operator intervention at each step, or certain steps may be automated. Automated steps may be performed by robotic devices which may communicate with neural release system 70 via wired or wireless communication channels. The automated steps may be completely automatic and implemented as a closed loop system with neural release system determining commands to be sent to the robotic devices which may control the expandable trial implant 300 and the cutting implement 594. The automated steps may be semi-automatic, requiring the surgeon or operator to acknowledge before proceeding with certain robotic steps.

Although the present invention has been described with reference to its preferred embodiments, those skillful in the art will recognize changes that may be made in form and structure which do not depart from the spirit of the invention.

We claim:

1. A method for spinal correction, comprising:
    inserting an expandable trial implant in an intervertebral disc space;

receiving load information from the expandable trial implant disposed in the intervertebral disc space, the implant being in a first expanded position after removal of a portion of the disc tissue;

comparing the load information to a load threshold;

indicating when the load information exceeds the load threshold;

receiving information representative of a neural foramen spacing from a neural spacing monitoring system, the neural foramen being located proximate the intervertebral disc space;

comparing the information representative of a neural foramen spacing to a predefined foramen spacing parameter; and determining whether to remove more of the disc based on comparison of the information representative of a neural foramen spacing and the predefined foramen spacing parameter.

2. The method of claim 1 wherein the receiving information representative of the neural foramen spacing comprises receiving information from an image guided surgery system.

3. The method of claim 1 wherein the receiving information representative of the neural foramen spacing comprises receiving information from a spinal pressure monitoring system.

4. The method of claim 1 wherein the receiving information representative of the neural foramen spacing comprises receiving information from a visualization system.

5. The method of claim 1 wherein the receiving information representative of the neural foramen spacing comprises receiving information from an ultrasonic detection system.

6. The method of claim 1 wherein the receiving information representative of the neural foramen spacing comprises receiving information from a balloon measurement system.

7. The method of claim 1 wherein the receiving load information from the expandable trial implant comprises receiving information from a plurality of load cells disposed on inferior and superior surfaces of the trial implant and mapping the load cell information from the load cells disposed on the inferior surface into at least two regions and mapping the load cell information from the load cells disposed on the superior surface into at least two regions.

8. The method of claim 1 wherein determining whether to remove more of the disc comprises determining where to remove more of the disc tissue based on at least one of the mapped regions of load information.

9. The method of claim 1 wherein determining whether to remove more of the disc comprises determining whether to remove more of the disc based on historical information of patient surgeries.

10. The method of claim 1 wherein determining whether to remove more of the disc comprises determining whether to remove more of the disc based on information representative of the neural foramen spacing received from a visualization system.

11. The method of claim 1 wherein determining whether to remove more of the disc comprises determining whether to remove more of the disc based on information received from a spinal pressure monitoring system.

12. The method of claim 1 wherein determining whether to remove more of the disc comprises determining whether to remove more of the disc based on information received from a balloon measurement system.

13. The method of claim 1 wherein determining whether to remove more of the disc comprises determining whether to remove more of the disc based on information received from an ultrasonic detection system.

14. The method of claim 1 wherein determining whether to remove more of the disc comprises determining whether to remove more of the disc based on information received from an image guided surgery system.

* * * * *